United States Patent [19]

Aranyi

[11] Patent Number: 5,478,347
[45] Date of Patent: Dec. 26, 1995

[54] ENDOSCOPIC SURGICAL INSTRUMENT HAVING CURVED BLADES

[75] Inventor: Ernie Aranyi, Easton, Conn.

[73] Assignee: United States Surgical Corporation, Norwalk, Conn.

[21] Appl. No.: 321,075

[22] Filed: Oct. 11, 1994

Related U.S. Application Data

[63] Continuation of Ser. No. 950,074, Sep. 23, 1992, abandoned, which is a continuation-in-part of Ser. No. 781,084, Oct. 18, 1991, abandoned, which is a continuation-in-part of Ser. No. 593,670, Oct. 5, 1990, abandoned.

[51] Int. Cl.⁶ .......................... A61B 17/32; A61B 17/36
[52] U.S. Cl. .......................... 606/170; 606/174; 606/167; 606/45; 606/46
[58] Field of Search .......................... 606/167, 170, 606/174, 175, 177, 179, 180

[56] References Cited

U.S. PATENT DOCUMENTS

| | | | |
|---|---|---|---|
| 115,735 | 6/1871 | Hughes | 606/174 |
| 487,068 | 11/1892 | Drinkwater. | |
| 856,927 | 6/1907 | Straw | 606/170 |
| 1,034,737 | 9/1912 | Dolan | 606/174 |
| 1,754,806 | 4/1930 | Stevenson. | |
| 2,002,594 | 5/1935 | Wappler et al.. | |
| 2,034,785 | 3/1936 | Wappler. | |
| 2,069,636 | 2/1937 | Wilson | 606/174 |
| 2,618,268 | 11/1952 | English. | |
| 2,790,437 | 4/1957 | Moore. | |
| 3,101,715 | 8/1963 | Glassman. | |
| 3,404,677 | 10/1968 | Springer. | |

(List continued on next page.)

FOREIGN PATENT DOCUMENTS

| | | |
|---|---|---|
| 0380874 | 8/1990 | European Pat. Off.. |
| 0484671 | 5/1992 | European Pat. Off.. |
| 2515564 | 6/1983 | France. |
| 8614855 | 4/1988 | France. |
| 840884 | 6/1952 | Germany. |
| 1065565 | 9/1959 | Germany. |
| 1566060 | 6/1970 | Germany. |
| 3013836 | 10/1981 | Germany. |
| 8900376 | 4/1989 | Germany. |
| 3802651 | 8/1989 | Germany. |
| 8903782 | 10/1989 | Germany. |
| 9106506 | 9/1991 | Germany. |
| 9109097 | 10/1991 | Germany. |
| 2086792 | 5/1982 | United Kingdom. |
| 8910093 | 11/1989 | WIPO. |
| 9102493 | 3/1991 | WIPO. |

OTHER PUBLICATIONS

Sklar Products, "Surgical Instruments: Suction and Pressure Apparatus," 1973, 18th ed., pp. 67 and 100.
Solos Endoscopy Brochure, "Instrument Set: Advanced Laparoscopic Surgical Devices".
Elmed Surgical Instruments Catalog 4 pages only.
Karl Storz Endoscope Operating Instruments Catalog 4 pages only.
Richard Wolf Medical Instruments Corp. Catalog 2 pages only.

*Primary Examiner*—David M. Shay

[57] ABSTRACT

An endoscopic surgical instrument having a handle assembly, a body portion, and a tool mechanism in which a pivoting handle pivots about a stationary handle to open and close the tool mechanism. The instrument includes a rotatable body portion, in which a rotation knob is provided on the instrument at the stationary handle so that the user may rotate the body portion, and consequently the tool mechanism, using a single hand. Furthermore, an electrocautery connection is provided which is positioned out of the line of sight of the surgeon, so that the surgeon may have an unobstructed view to the surgical site. The pivoting handle is provided with a rotatable connection point for connecting the slidable rod member to essentially eliminate radial deflection of the rod within the outer tube during opening and closing of the handles. The instrument also includes crescent-shaped blades which are curved in a plane defined by the pivot axis of the blades and the longitudinal axis of the instrument.

24 Claims, 20 Drawing Sheets

U.S. PATENT DOCUMENTS

| | | |
|---|---|---|
| 3,446,211 | 5/1969 | Markham . |
| 3,585,985 | 6/1971 | Gould . |
| 3,735,763 | 5/1973 | Shannon et al. . |
| 3,807,406 | 4/1974 | Rafferty et al. . |
| 3,840,003 | 10/1974 | Komiya . |
| 3,871,379 | 3/1975 | Clarke . |
| 3,895,636 | 7/1975 | Schmidt . |
| 3,964,468 | 6/1976 | Schulz . |
| 3,995,619 | 12/1976 | Glatzer . |
| 4,005,714 | 2/1977 | Hildebrandt . |
| 4,038,987 | 8/1977 | Komiya . |
| 4,043,343 | 8/1977 | Williams . |
| 4,049,002 | 9/1977 | Kletschka et al. ............ 606/174 |
| 4,054,143 | 10/1977 | Bauer . |
| 4,064,881 | 12/1977 | Meredith . |
| 4,122,856 | 10/1978 | Mosior et al. . |
| 4,128,099 | 12/1978 | Bauer . |
| 4,169,476 | 10/1979 | Hiltebrandt . |
| 4,201,213 | 5/1980 | Townsend . |
| 4,243,047 | 1/1981 | Olsen . |
| 4,282,884 | 8/1981 | Boebel . |
| 4,345,589 | 8/1982 | Hiltebrandt . |
| 4,369,788 | 1/1983 | Goald . |
| 4,433,687 | 2/1984 | Burke et al. . |
| 4,474,174 | 10/1984 | Petruzzi . |
| 4,512,343 | 4/1985 | Falk et al. . |
| 4,522,206 | 6/1985 | Whipple et al. . |
| 4,569,131 | 2/1986 | Falk et al. . |
| 4,572,185 | 2/1986 | Rich . |
| 4,574,802 | 3/1986 | Straub et al. . |
| 4,590,936 | 5/1986 | Straub et al. . |
| 4,643,190 | 2/1987 | Heimberger . |
| 4,646,751 | 3/1987 | Maslanka . |
| 4,662,371 | 5/1987 | Whipple et al. . |
| 4,669,470 | 6/1987 | Brandfield . |
| 4,669,471 | 6/1987 | Hayashi . |
| 4,674,501 | 6/1987 | Greenberg . |
| 4,712,545 | 12/1987 | Honkanen . |
| 4,721,116 | 1/1988 | Schintgen et al. . |
| 4,759,364 | 7/1988 | Boebel . |
| 4,763,668 | 8/1988 | Macek et al. . |
| 4,763,669 | 8/1988 | Jaeger . |
| 4,785,825 | 11/1988 | Romaniuk et al. . |
| 4,819,633 | 4/1989 | Bauer et al. . |
| 4,872,456 | 10/1989 | Hasson . |
| 4,877,026 | 10/1989 | de Laforcade . |
| 4,881,550 | 11/1989 | Kothe . |
| 4,887,612 | 12/1989 | Esser et al. . |
| 4,896,678 | 1/1990 | Ogawa . |
| 4,898,157 | 2/1990 | Messroghli et al. . |
| 4,919,152 | 4/1990 | Ger . |
| 4,938,214 | 7/1990 | Specht et al. . |
| 4,944,093 | 7/1990 | Falk . |
| 4,950,273 | 8/1990 | Briggs . |
| 4,976,723 | 12/1990 | Schad . |
| 4,986,825 | 1/1991 | Bays et al. . |
| 4,994,024 | 2/1991 | Falk . |
| 5,009,661 | 4/1991 | Michelson . |
| 5,052,402 | 10/1991 | Bencini et al. . |
| 5,133,727 | 7/1992 | Bales et al. . |
| 5,141,519 | 8/1992 | Smith et al. . |
| 5,152,780 | 10/1992 | Honkanen et al. . |
| 5,171,256 | 12/1992 | Smith et al. . |
| 5,171,258 | 12/1992 | Bales et al. . |
| 5,320,636 | 6/1994 | Slater . |

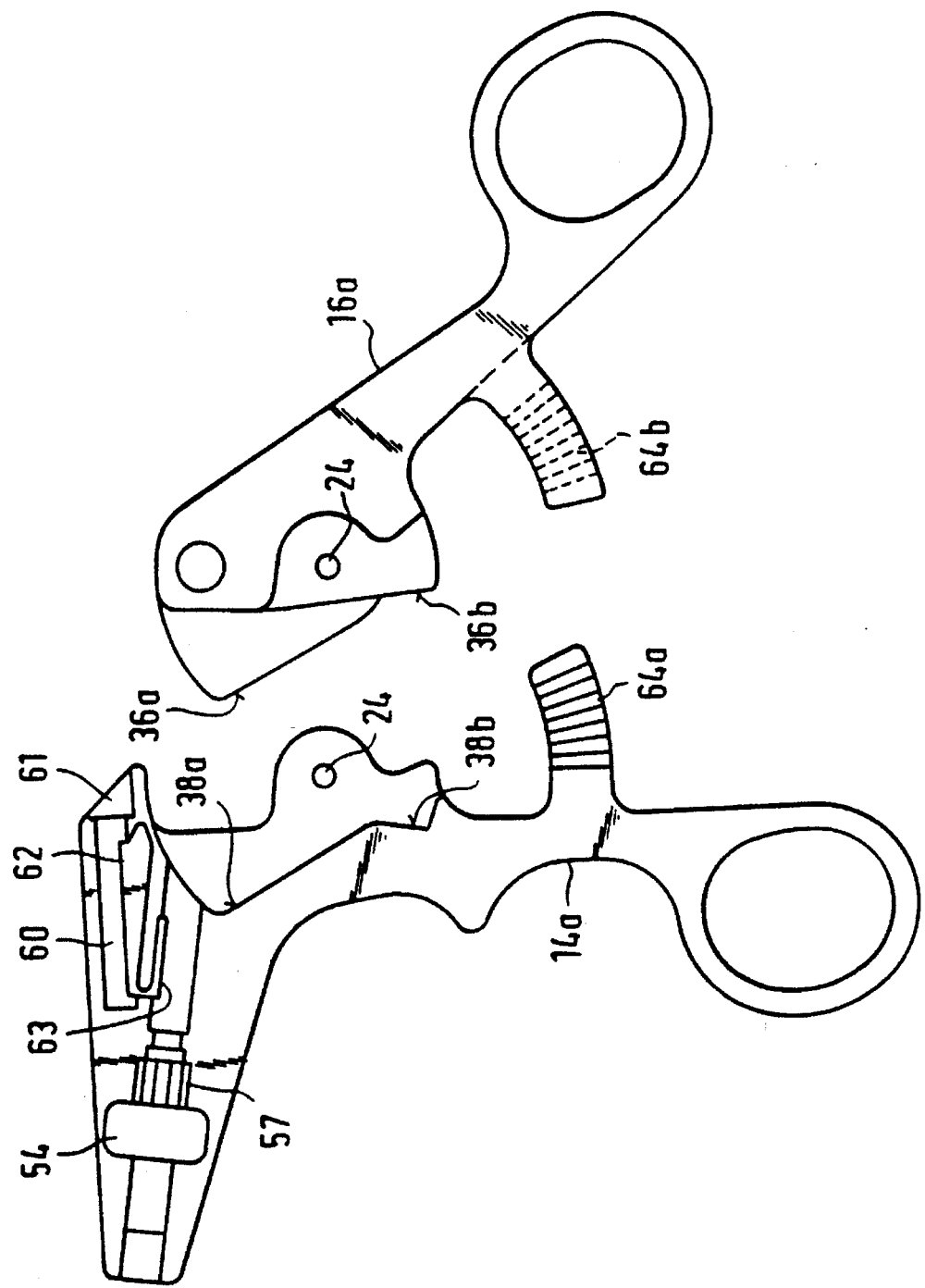

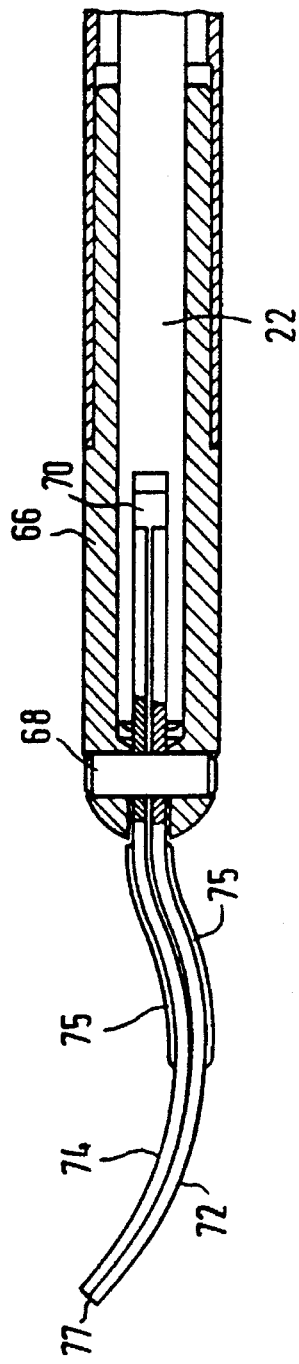
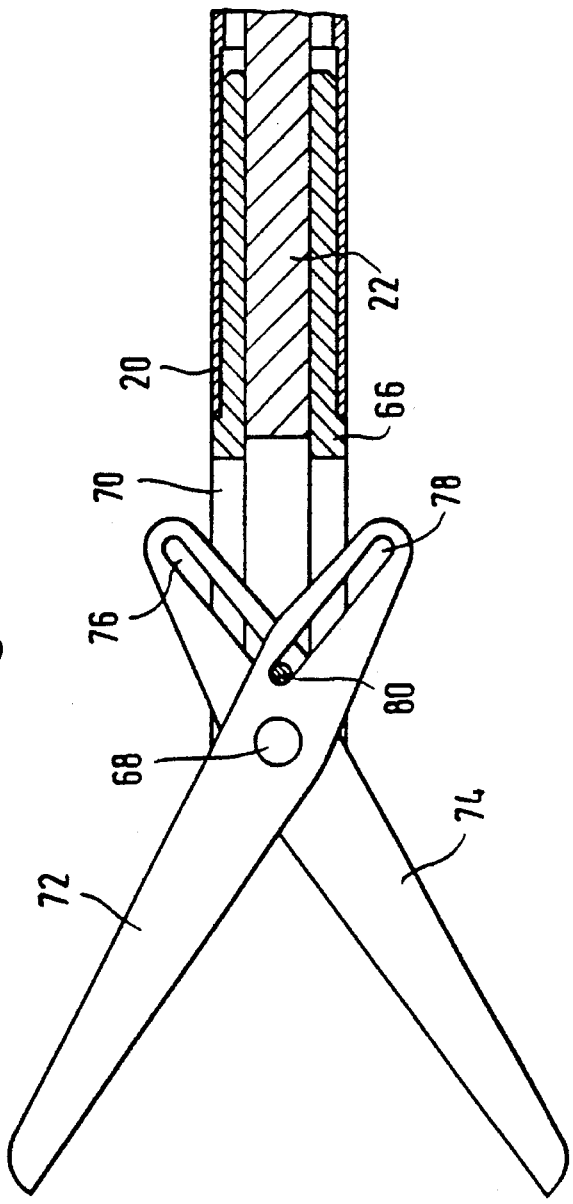

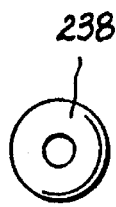
FIG.28a    FIG.28b
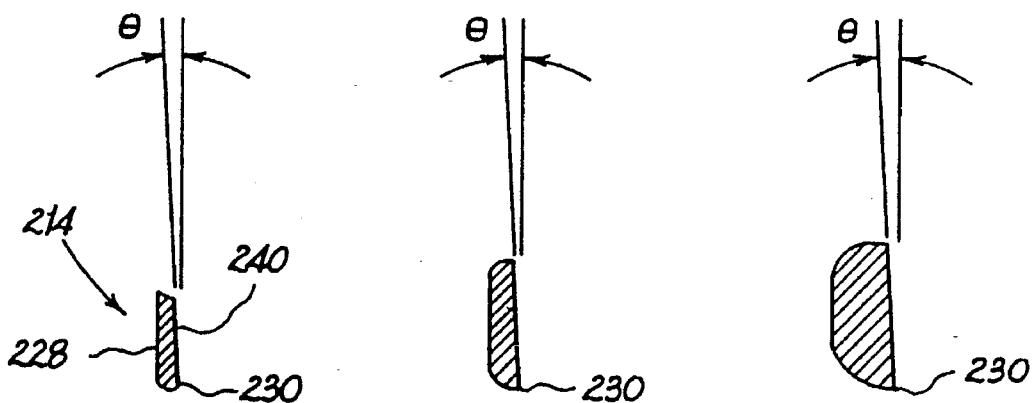
FIG.29a    FIG.29b    FIG.29c
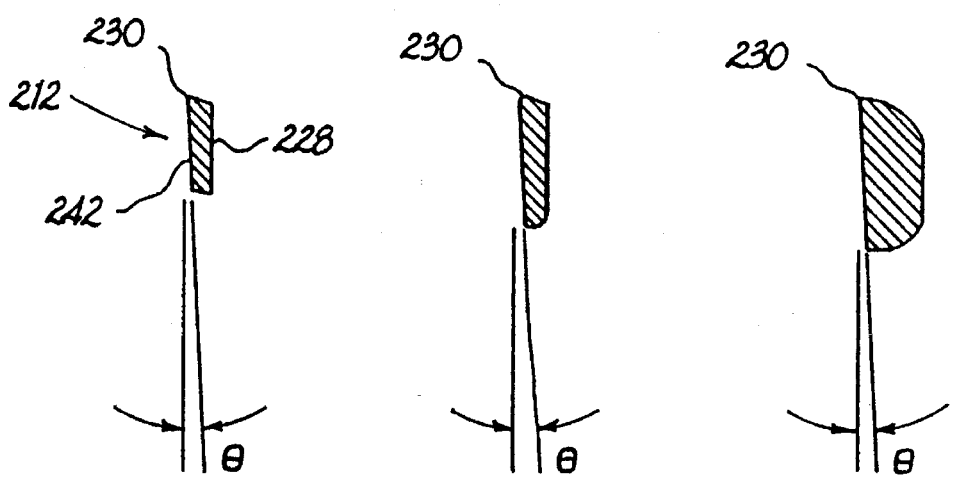
FIG.30a    FIG.30b    FIG.30c

ENDOSCOPIC SURGICAL INSTRUMENT HAVING CURVED BLADES

CROSS REFERENCE TO RELATED APPLICATION

This is a continuation of application Ser. No. 07/950,074, filed on Sep. 23, 1992, now abandoned, which is a continuation-in-part of prior application Ser. No. 07/781,064, filed Oct. 18, 1991, now abandoned, which is a continuation-in-part of prior application Ser. No. 07/593,670, filed Oct. 5, 1990 now abandoned.

BACKGROUND OF THE INVENTION

1. Field of the Invention

The present invention relates to endoscopic surgical instruments, and more particularly relates to an endoscopic instrument having reciprocating jaw members which pivot in response to the opening and closing of a handle member, where the movement of the handles is translated through an elongated tubular body member to open and close the jaw mechanism.

The present invention further provides a device in which the jaw mechanism may comprise cutting scissor blades, a gripping device for holding tissue during surgery, holding surgical needles and the like. The device of the present invention may be provided with a rotatable tubular body for selectively positioning the angle at which the jaw mechanism operates, and provision is also made for the use of electrocautery capabilities to provide for cauterization at the surgical site.

2. Discussion of the Prior Art

In the prior art, various endoscopic surgical instruments are disclosed which utilize generally complex mechanisms for opening and closing handle members and jaw members to facilitate use of the device at a surgical site. Many devices provide an intricate construction in which a linkage mechanism for opening and closing the jaws requires numerous moving parts, while a sliding arrangement is provided between two extended rod members which activates the linkage mechanism in response to movement of the handle members. In addition, pivoting of the handle members in many cases causes an unwanted radial torquing force on the rod which requires additional space to be provided in the handle members to accommodate the radial movement of the rod.

Endoscopic devices presently in use include many devices having an interchangeable shaft assembly and jaw mechanism in which a common reusable handle may be used with a series of instruments. However, these devices suffer disadvantages in that the connecting mechanism oftentimes obstructs the view of the surgeon, and the integrity of the device may be decreased due to loosening of the connection. These disadvantages are critical due to the fact that an endoscopic surgical procedure requires precision instruments with tolerances that are carefully monitored. As the connections wear, precision is sacrificed, and the usefulness of the tool is diminished.

Greenberg, U.S. Pat. No. 4,674,501 discloses a surgical instrument having a pair of reciprocating shafts which are provided with a rotational indexing knob in which the shafts are allowed to rotate to position a cutting tool at a specific angle to the handles. The shafts slide on top of each other in response to opening and closing of the handle members to open and close the jaw members of the cutting instrument. The housing is secured to a stationary handle, such that the shaft assembly rotates with the indexing knob. One shaft is secured in a ball and socket joint to a movable handle which facilitates the sliding arrangement of the movable shaft over a stationary shaft. The handle assembly is disengagable from the housing by means of a screw, and the ball joint slides out of the socket to remove the handles. This type of device is subject to the disadvantage disclosed above, in which the integrity of the device is compromised due to the number of moving parts, as well as to the fact that the ball and socket joint is an inherently loose connection which will deteriorate during continued use.

Ger, U.S. Pat. No. 4,919,152, discloses a clip applying device having a stationary handle and a pivoting handle to which an elongated shaft arrangement is attached. At the end of the shaft is a pair of reciprocating jaw members which are operated in response to pivoting movement of the handles. An inner shaft member is attached to the pivoting handle, the shaft member passing through an outer tube member which is attached to the stationary handle. As the rod member passes through the stationary handle, as well as through the outer tube at the location it is attached to the stationary handle, radial movement of the rod within the outer tube must be accounted for since the rod is attached to the stationary handle at a non-movable point. In relation to this, the bushing member is necessary inside the stationary handle to accommodate the radial play in the rod member during opening and closing of the handles.

Straub et al., U.S. Pat. No. 4,590,936, discloses a microsurgical instrument having a complex gear mechanism for translating movement of the handles to an opening and closing movement of the jaw members. A helical slot is provided in a shaft member which allows a pin to move through the slot to move the jaw members. Furthermore, a ball and socket joint is provided in the movable handle to connect the movable handle to the inner rod.

Bauer, U.S. Pat. No. 4,128,099, discloses a forceps device having an attachment for cauterization which conducts current through the outer tube to the jaw mechanism. A complex insulation system is provided to insulate the handle from the shaft, as well as to insulate the shaft itself. This device suffers the disadvantage that in order to insulate the handle, the rod member is secured to an insulating bushing, and a second rod is provided to the bushing to connect to the handle members. Furthermore, the connection point for the electrical connector is positioned in an area which will obstruct the view of the surgeon as he looks down the device to a surgical site.

Endoscopic surgical instruments are known in the art which include cooperating cutting blade members. Typically, in such an instrument, a gap between the blade portions is evident when the blades are engaged for cutting. For some surgical procedures a gap between the blades is undesirable because it detrimentally affects cutting precision. Thus, the surgeon cannot achieve the clinical results desired, and in some cases, for example, ripping or tearing of tissue may occur.

Moreover, prior art endoscopic surgical instruments are known to suffer from undesirable splaying of the blade members. Normally, at least one blade member is movably attached to a pivot point. When the blade members are repeatedly used, or encounter a hard substance during use, the blade members will tend to move laterally apart from one another, or splay. Blade member splaying increases the gap between the blade surfaces, and detrimentally affects cutting ability and precision.

Further, an undesirable feature of prior art endoscopic surgical instruments occurs when the blade members extend past the desired closed position becoming "overstroked." To clarify, blade overstroke occurs when the blade surface of at least one movable blade member surpasses the desired closed cutting position of the reciprocating blade.

The novel endoscopic surgical instrument pursuant to the present invention obviates the disadvantages encountered in the prior art and provides a precise instrument which is easy to manufacture and efficient to use, which eliminates many of the moving parts required by prior art devices. The instrument of the present invention incorporates many features which are of use to the surgeon during an operation, while it maintains a lightweight construction in an easy to handle device in which all the features may be operated with one hand. Furthermore, the features are so positioned so as to provide a maximum line of sight for the surgeon without obstructing the view to the surgical site.

SUMMARY OF THE INVENTION

The present invention provides a novel endoscopic surgical device which incorporates many features necessary for an endoscopic surgical procedure, and provides a lightweight and easy to use device which may be operated with one hand. The device is simple to manufacture, and may incorporate any one of a series of jaw mechanisms for various surgical procedures. The device is a high precision instrument in which many moving parts normally associated with such a device are eliminated, thus reducing instances of mechanical failure requiring expensive repair or ultimate destruction of the instrument.

The endoscopic surgical instrument of the present invention essentially consists of a handle assembly, an elongated body assembly, and a tool mechanism attached at a distal end of the body assembly remote from the handle assembly. The handle assembly includes a stationary handle and pivoting handle, whereby the body assembly is attached to the stationary handle assembly and extends therefrom. The body assembly consists of an outer tubular member and an inner rod member which coaxially passes within the outer tubular member. The rod member is attached to the pivoting handle, while the tube member is secured in a conventional manner to the stationary handle. Preferably, the outer tube is provided with a detent which cooperates with a boss on the interior of the stationary handle to lock the outer tube in place. As the pivoting handle moves, the rod member slidably reciprocates within the outer tube member.

Attached to a distal end of the body assembly is provided the tool mechanism which opens and closes in response to movement of the pivoting handle in relation to the stationary handle. The tool mechanism may comprise a pair of jaw members wherein one or both jaw members open and close to perform various endoscopic surgical procedures. The jaw mechanism includes, but is not limited to, a scissor device, a dissecting device, a grasping device and the like.

In one embodiment the jaw mechanism is secured to the outer tubular member by means of a transverse post member which serves as a common pivot point about which both jaw members pivot. Each jaw member is provided with a camming portion which extends away from the pivot point, and consists of a cam slot which extends from the pivot point into the outer tube. The upper jaw is generally provided with a pair of spaced apart projections, each provided with a cam slot which transversely overlap each other. The lower jaw is also provided with a pair of extensions which are spaced apart a distance which is less than the space between the projections of the upper jaw member so that the lower projections pass between the upper projections. The lower projections are also provided with transverse overlapping slots which are positioned at an angle to the upper cam slots. However, each jaw may be provided with a single projection particularly if the jaw comprises a scissor blade. The jaw mechanism is secured to the outer rod through the common pivot point.

The inner rod member is provided with a bearing surface, which typically comprises a post member which passes through and is engaged within the cam slots of both jaw members. As the pivoting handle is moved, the rod slides through the outer tube and causes the post member to bear on the camming slots to pivot the jaw members about the common pivot point to open the jaw members. Since the cam slots are at an angle to each other, movement of the post member through the slots pivots both jaw members as the post rides through the slots. As the rod reciprocates, the jaw mechanism opens and closes.

In order to prevent excessive forces from being applied to the jaw mechanism, the pivoting handle is provided with a pair of stop members which are positioned proximate the pivot point which secures the pivoting handle to the stationary handle, and about which the pivoting handle moves. The upper, or proximal stop member abuts a boss within the stationary handle to prevent the jaw mechanism from opening too wide, while a distal, or lower stop member abuts the stationary handle to prevent excessive forces from being applied to the jaw mechanism during closing. Accordingly, the application of force to the jaw mechanism may be regulated during design and manufacture by the interengagement of the stop members on the pivoting handle with the bosses on the stationary handle.

A novel feature of the present invention is the provision of a second pivot point on the pivoting handle, to which the inner rod member is attached. As the handle pivots, the second pivot point rotates to allow the inner rod to move longitudinally in the outer tube with minimal radial deflection. This is an important feature of the present invention in that it reduces the radial wear on the inner rod and prevents weakening of the structure during long term use. In addition, it allows for a reduction of the required internal spacing between the outer tube and the inner rod to result in a more compact and streamlined instrument. Furthermore, unwanted torquing forces are eliminated at the pivot point thus minimizing the possibility of mechanical breakdown of the instrument at the connection between the pivoting handle and the movable inner rod.

The present invention may also feature a connection port to provide the device with electrocautery capabilities. In this embodiment of the invention, a connection port is provided, preferably on the stationary handle on the side of the longitudinal axis opposite the finger grip portion. The connection port is positioned at an angle to the longitudinal axis, which is preferably less than 30° and in a preferred embodiment is approximately 9° to the longitudinal axis, and extends in a direction away 0 from the body assembly. In this way, the surgeon's line of sight is unobstructed and provides a clear view to the surgical site. The connection port allows for the connection of a suitable jack member to be inserted into the device. Electrical connection between the port and the outer tube is provided by a leaf spring member which extends from the port area to the outer tube. The outer tube is provided with electrical insulation, preferably heat shrink tubing, which extends a substantial portion of the length of the outer tube. In this embodiment, the handle is molded of plastic material to provide electrical insulation to the user.

It is also contemplated that the electrical port connection may be provided adjacent the finger grip of the stationary handle, so that the jack member extends downwardly away from the device to insure an unobstructed line of vision for the surgeon. In this case, a leaf spring member extends from the port through the stationary handle to the outer tube to complete the electrical connection.

A further feature of the present invention is the provision of a rotatable knob on the outer tubular member to allow the body assembly and the jaw mechanism to rotate to position the jaws at desired angles to the longitudinal axis during the surgical procedure. Preferably, the rotatable knob is secured to the outer tube and positioned in a slot which passes through the stationary handle, so that a surgeon may rotate the knob, and consequently the body assembly and jaw mechanism, through the use of his thumb while he is holding the stationary handle with his fingers. This frees the surgeon's other hand to simultaneously operate another instrument during surgery.

Preferably, the rotatable knob is secured to a bushing, which in turn is secured to the outer tube member. The bushing is provided with a polygonal cross-section, which corresponds to a boss member within the interior of the stationary handle. This allows for incremental rotation of the body assembly and jaw mechanism to desired angles to the longitudinal axis. Preferably, the bushing has a dodecahedral cross-section.

In a preferred embodiment, all the above features are incorporated into a single endoscopic surgical instrument, so that the instrument has electrocautery and rotational capabilities. However, the instrument may be constructed without one or more of the features while still providing a lightweight precision instrument.

Another embodiment of the present invention provides, an endoscopic surgical instrument including a handle assembly, and a body assembly including an outer tube member and a rod member cooperating with the handle assembly. A tool mechanism includes a pair of reciprocating members pivotally secured to a distal end of the body assembly cooperating with the handle assembly.

The reciprocating members of the tool mechanism include a blade portion which each have a blade edge, and in a preferred embodiment, at least one of the blade edges includes an inflected surface. The inflected surface substantially closes a gap between the cooperating blade surfaces. The enhanced cooperation between the blade surfaces enables the surgeon to meet critical tolerances in surgical operations, and provides a precision shearing action to cut tissue.

The endoscopic surgical instrument further provides a tube portion at a distal end of the body assembly. The tube portion substantially prevents the reciprocating members from laterally separating.

The endoscopic surgical instrument also provides an abutment member coupled to at least one of the reciprocating members. The abutment member cooperates with the outer tube member of the body assembly. The mutual cooperation between the abutment member and the outer tube member discourages the closed reciprocating members from becoming overstroked.

Another embodiment of the present invention provides a cutting mechanism for shearing tissue in which the cutting mechanism is particularly suited for shearing thick tissue and for use in endoscopic surgical procedures where it may be necessary to cut staples or sutures inside the patient's body. The cutting mechanism is for use with an endoscopic surgical instrument which includes the handle mechanism and elongated body portion as described above, and preferably includes a pair of crescent shaped blade members which taper in thickness from the connection point at the body assembly to the tip of the cutting mechanism. The crescent shaped blade members are positioned in overlapping relation and preferably have different radii of curvature relative to the pivot point so that when the cutting mechanism is constructed the blades contact each other at a single point along the cutting edge to enhance the shearing effect of the scissors and to reduce the incidence of the blades separating during cutting. While the radii of curvature may be the same at the cutting edge surface of each blade member, when the cutting mechanism is assembled the radii of curvature for the two blade members are different relative to the pivot point. The blade members preferably are metal injection molded and then ground to provide a precision cutting edge surface on the blade members. A further feature of the cutting mechanism of the present invention is the provision of a relief angle on the surface of the blade members that face each other where that surface is angled toward the cutting edge to further enhance the shearing effect. The relief angle is formed during grinding of the blade member.

Accordingly, it is an object of the present invention to provide an endoscopic surgical instrument in which all the features may be used by a surgeon with one hand.

It is another object of the present invention to provide a lightweight endoscopic surgical instrument which provides a clear line of sight for a surgeon during a surgical procedure.

It is a further object of the present invention to provide an endoscopic surgical instrument which prevents the application of excessive forces to the working tool mechanism to prevent damage to the instrument, whether the tool mechanism is being opened or closed.

It is yet a further object of the present invention to provide an endoscopic surgical instrument in which tolerances between the inner slidable rod member which operates the jaws and the outer tubular member which holds the jaw mechanism are such that there is little or no radial deflection of the rod during longitudinal movement through the tube.

It is still a further object of the present invention to provide an endoscopic surgical instrument having a handle assembly in which a first pivot point is provided for pivoting the movable handle about the stationary handle and a second pivot point is provided which connects the movable rod member to the pivoting handle which allows for rotation of the second pivot point to prevent radial deflection of the rod during longitudinal movement.

It is yet another object of the present invention to provide an endoscopic surgical instrument having electrocautery capabilities in which the connection port for an electrical jack member is out of the line of sight of the surgeon during use.

It is still a further object of the present invention to provide an endoscopic surgical instrument having a rotatable body member and jaw mechanism in which the rotation may be accomplished by the surgeon while using one hand.

It is still another object of the present invention to provide an endoscopic surgical instrument having all the features above including a rotatable body assembly and jaw mechanism, electrocautery capabilities, and a rotatable pivot point for connecting the inner rod to the pivot handle to prevent radial deflection of the rod during longitudinal movement.

It is another object of the present invention to provide an endoscopic surgical instrument that provides cooperating blade surfaces that substantially eliminate a gap therebetween.

It is a further object of the present invention to provide an endoscopic surgical instrument that provides a device for discouraging the blade members from splaying.

It is yet a further object of the present invention to provide an endoscopic surgical instrument that provides a device for discouraging the blade members from becoming overstroked.

It is still another object of the present invention to provide an endoscopic cutting instrument which includes a cutting mechanism having an enhanced cutting surface which is capable of cutting thick tissue, as well as staples, sutures and the like, and being further capable of cutting thin or delicate tissue after cutting the thick tissue, staples or sutures during a surgical procedure.

BRIEF DESCRIPTION OF THE DRAWINGS

The foregoing objects and other features of the invention will become more readily apparent and may be understood by referring to the following detailed description of an illustrative embodiment of the endoscopic surgical instrument, taken in conjunction with the accompanying drawings, in which:

FIG. 5 illustrates a side cutaway view of a handle of a preferred embodiment of an endoscopic surgical instrument according to the present invention;

FIG. 6A shows a top cutaway view of the tool mechanism of an endoscopic surgical instrument according to the present invention;

FIG. 6B illustrates a side cutaway view of the tool mechanism of FIG. 6A of an endoscopic surgical instrument according to the present invention;

FIGS. 28A and 28B illustrate a top plan view and a side plan view, respectively, of a spring washer for use with the cutting mechanism of the present invention;

FIGS. 29A through 29C illustrate cross-sectional views of the blade member of FIG. 27A taken along lines 29A—29A, 29B—29B, and 29C—29C, respectively;

FIGS. 30A through 30C illustrate cross-sectional views of the blade member of FIG. 26A taken along lines 30A—30A, 30B—30B, and 30C—30C, respectively;

DETAILED DESCRIPTION OF THE PREFERRED EMBODIMENTS

Figure 1:
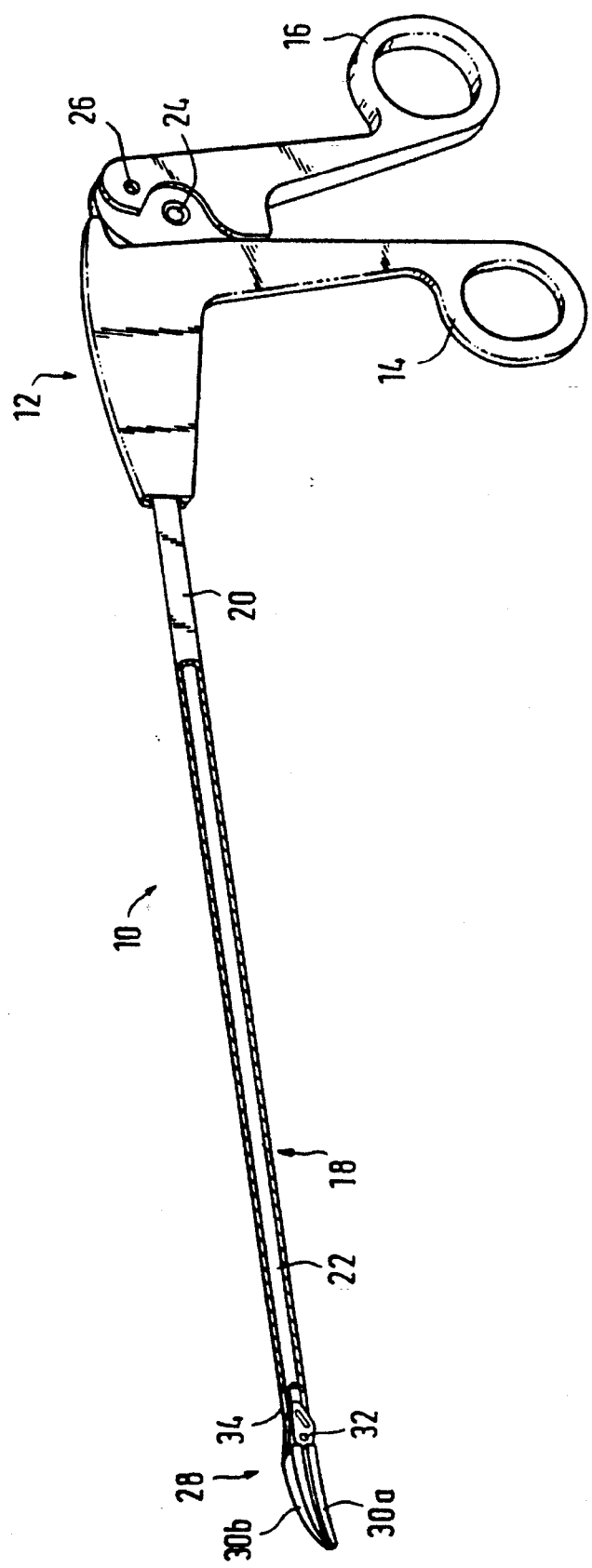
FIG. 1 illustrates a perspective view of an endoscopic surgical instrument in partial cutaway according to the present invention.

Referring now in specific detail to the drawings, in which like reference numbers identify similar or identical elements, FIG. 1 illustrates an embodiment of the endoscopic surgical instrument 10. In its simplest form, the device comprises a handle assembly 12 which consists of a stationary handle 14 and a pivoting handle 16. Extending from the handle assembly is a body portion 18 which comprises an outer tubular member 20 through which a slidable inner rod member 22 passes in coaxial relationship. The outer tube 20 is secured to the stationary handle 14, while the inner rod 22 is secured to pivoting handle 16 at rotatable connection point 26. Handle 16 pivots about pivot point 24 to move in relation to stationary handle 14.

Attached at a distal end of the body portion 18 is a tool mechanism 28, which essentially consists of a lower jaw member 30A and an upper jaw member 30B. The tool mechanism is connected to the body portion 18 at pivot point 32 and moves in a reciprocating manner about pivot point 32 through the provision of linkage mechanism 34. Linkage mechanism 34 will be described in greater detail below.

In use, as pivoting handle 16 pivots about pivot point 24 in relation to stationary handle 14, inner rod 22 reciprocatingly slides within outer tube 20 in response to the push or pull force at connection point 26. The function of connection point 26 will be described in greater detail below.

As rod 22 slides within tube 20, the linkage mechanism 34 is actuated to pivot jaw members 30A and 30B about pivot point 32 to open and close the members. Jaw members 30A and 30B may comprise scissors, dissecting jaws, or a grasping mechanism, or any other tool mechanism required for specific surgical procedures.

Figure 2:
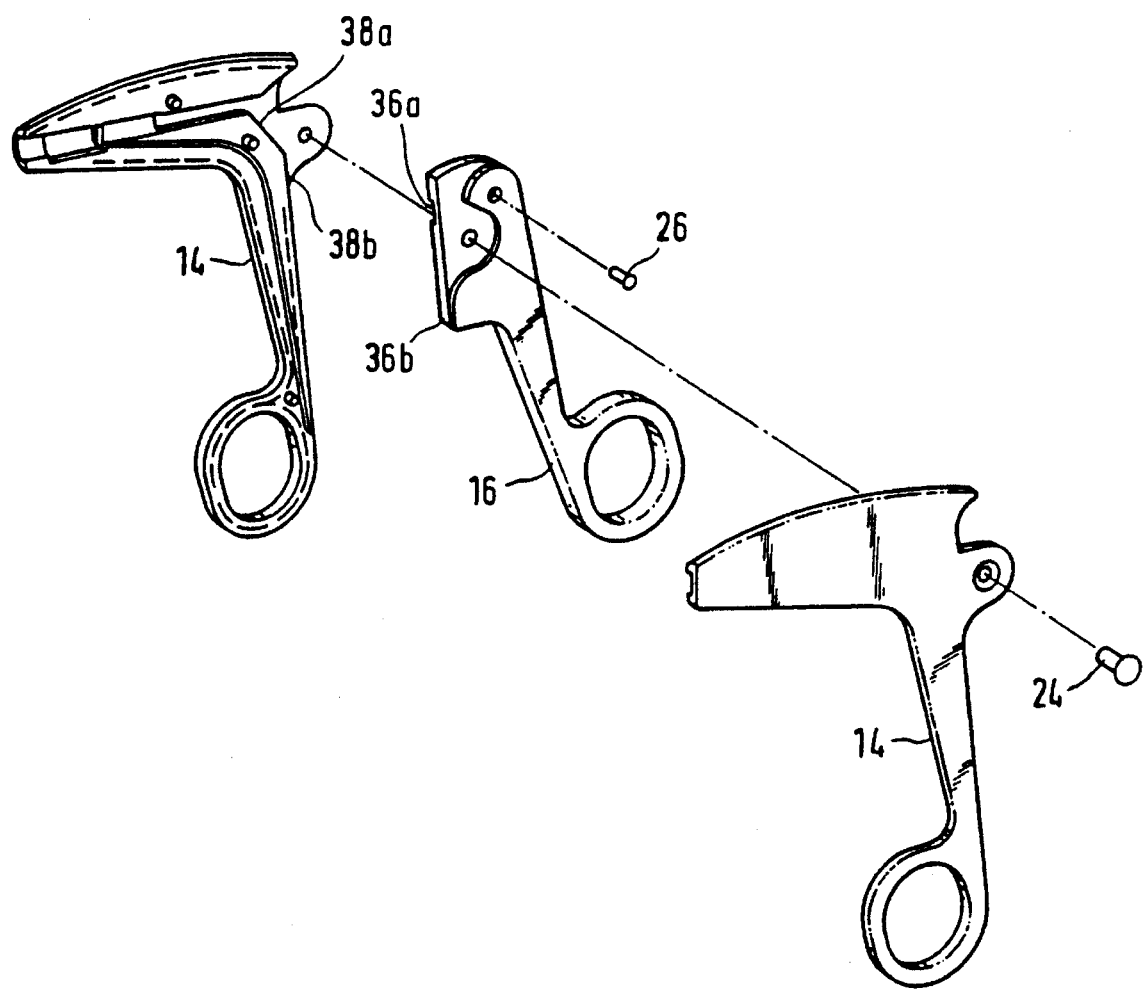
FIG. 2 illustrates an exploded perspective view of a handle of an endoscopic surgical instrument according to the present invention.

As best seen in FIG. 2, pivoting handle 16 is provided with a pair of stop members 36A and 36B which cooperate with boss members 38A and 38B, respectively, to limit the rotational movement about pivot point 24 of the pivoting handle 16. The stop members are positioned on opposite sides of pivot point 24 so that when pivoting handle 16 is moved away from stationary handle 14, proximal stop 36A contacts boss 38A to limit the actual rotation of handle 16.

When handle 16 is moved towards handle 14, distal stop 36B contacts boss 38B to limit the rotation of handle 16 in that direction. The stop members are provided to prevent the application of excessive forces on the tool mechanism during opening and closing of the surgical instrument. In this manner, the possibility of damage or destruction of the tool mechanism is greatly reduced or eliminated.

Figure 3:
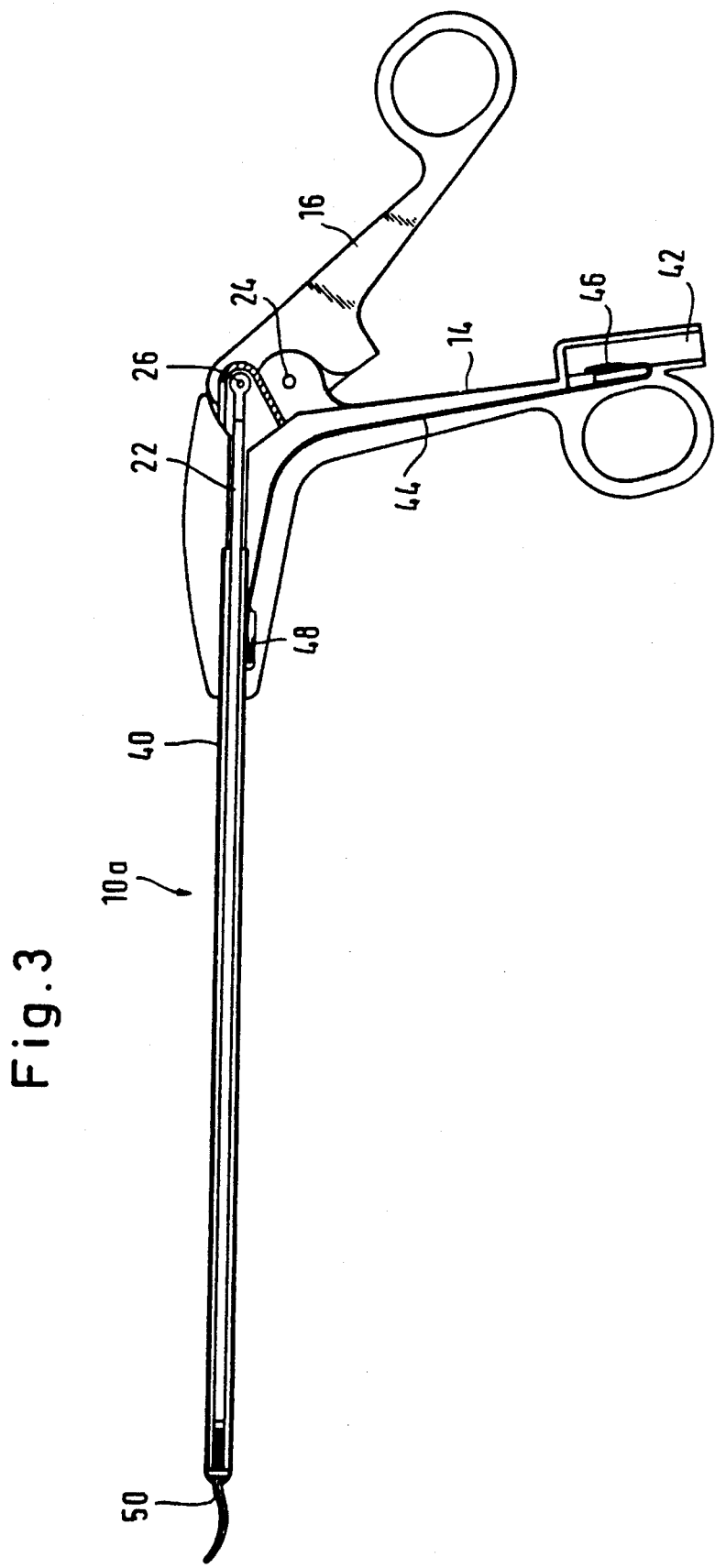
FIG. 3 illustrates a side cutaway view of an alternate embodiment of an endoscopic surgical instrument according to the present invention.

Turning now to FIG. 3, FIG. 3 illustrates a first alternate embodiment 10A of the endoscopic surgical instrument of the present invention. Instrument 10A is similar to instrument 10 except for the provision of an electrocautery connection to allow for cauterization of tissue at the surgical site during the surgical procedure. Stationary handle 14 is provided with a connection port 42 for the reception of an electrical jack member (not shown) for providing the necessary current to the tool. A leaf spring 44 electrically connects port 42 with outer tube member 20 which carries the electric current to the tool mechanism at the surgical site. The leaf spring is provided with a connection member 46 at the port 42 and a connection member 48 at the outer tube. The connection members essentially rely on the resiliency of the material which comprises the leaf spring, but of course may be any conventional electrical connection.

As the electrical charge is applied to the outer tube, it conducts along the outer tube to the tool mechanism, which in this instance is preferably a scissor device 50 or other tool mechanism such as cautery hooks, forceps, or the like. In order to protect the surgeon who is using the device from electrical shock, the handle is preferably constructed of a rigid plastic material which renders the device lightweight and electrically insulated.

In order to prevent electrical shock during use, an insulation member 40 is provided on outer tube 20, the insulation member preferably consisting of heat shrink tubing. Heat shrink tubing 40 passes into stationary handle 14 to prevent the possibility of electric shock.

While connection port 42 is shown as being attached to stationary handle 14 at the finger grip, it is also contemplated to position the connection port on top of the handle as shown and described below in relation to FIG. 5. The positioning of the connection port in the present invention is such so as to provide the surgeon with an unobstructed line of sight down body member 18 to view the surgical site at the tool mechanism 28.

Figure 4:
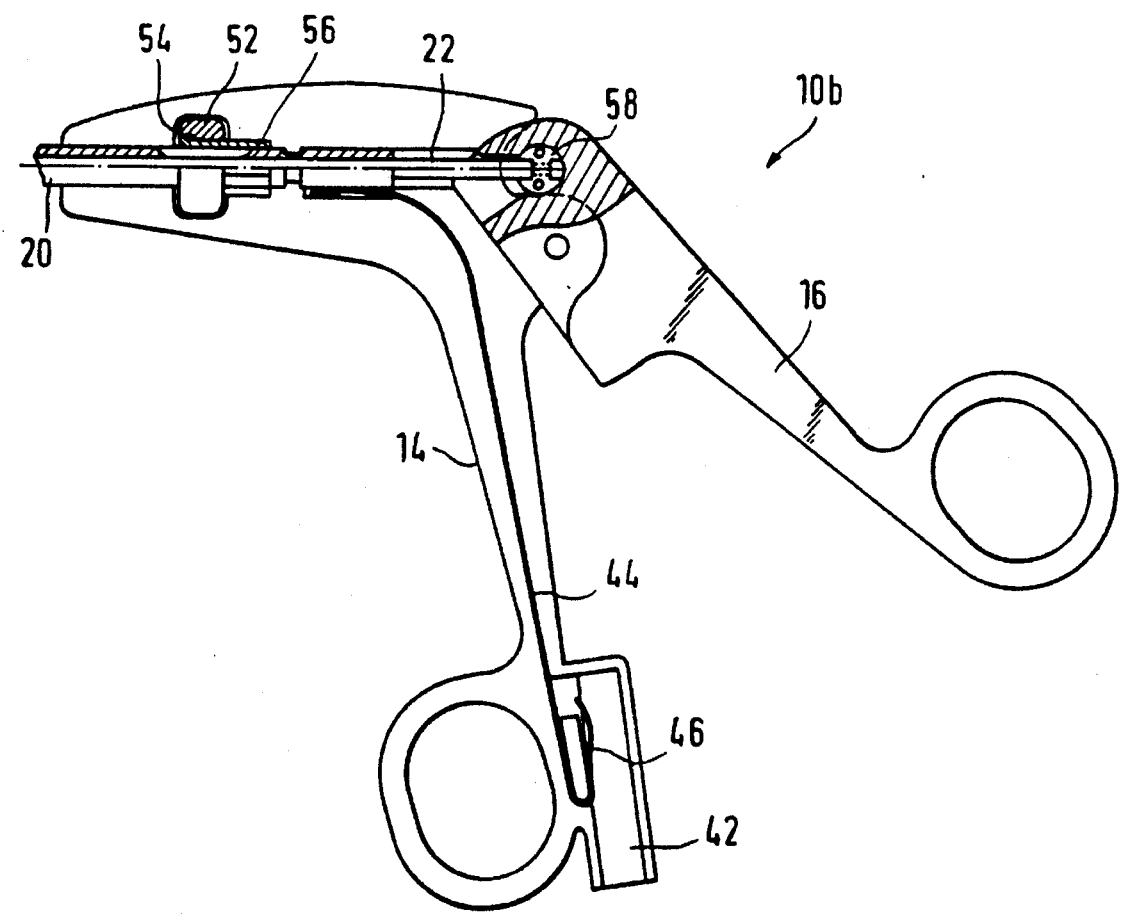
FIG. 4 illustrates a side cutaway view of a second alternate embodiment of an endoscopic surgical instrument according to the present invention.

FIG. 4 illustrates a preferred embodiment of the invention, in which the instrument 10B is provided with the electrocautery feature as well as having provisions for a rotatable body portion 18. As seen in FIG. 4, a slot 54 is provided in stationary handle member 14 which passes completely through the handle member. Positioned within the slot 54 is a rotatable knob 52 which is fixedly secured to outer tube 20 through the provision of a bushing member 56. The rotatable knob 52 and bushing member 56 will be described in greater detail below.

Also as best seen in FIG. 4, inner rod member 22 is connected to pivoting handle 16 through the provision of a rotational bushing 58. Bushing 58 pivots during movement of pivoting handle 16 so that as rod member 22 is reciprocated within tube 20, the bushing member 58 rotates to minimize or eliminate any radial movement of rod 22, to insure that rod 22 moves in a longitudinal direction only. This alleviates excessive torquing forces on rod member 22 as well as unwanted excessive forces at the connection point 26 to prevent damage to the handle or the inner rod member 22. Another feature provided by this rotational bushing member 58, is that by greatly reducing or eliminating radial movement of rod member 22, exact tolerances between the outer tube 20 and the inner rod member 22 may be maintained, so that less spacing is required and the instrument may be made in a smaller size than conventional endoscopic instruments. In addition, by greatly reducing or eliminating the radial deflection, the precision of the instrument is greatly enhanced. The features of rotational bushing member 58 will be described in greater detail below.

Turning now to FIG. 5, stationary handle 14A and pivoting handle 16A are illustrated having the provision of a locking mechanism 64A and 64B. FIG. 5 shows handle member 14A in a side cutaway view, and is the preferred embodiment of the present invention. As clearly seen in this view, handle member 14A and handle member 16A are attached at pivot point 24 so that during opening and closing of the handle assembly, proximal stop member 36A contacts boss 38A to limit rotation of pivoting handle 16A away from stationary handle 14A. When the handles are moved towards each other, stop member 36B contacts boss member 38B to limit rotation in that direction. Locking mechanism 64A and 64B may be utilized to position the handles at various locations during the opening and closing procedure, which of course allows for the application of various closing forces on the tool mechanism at the distal end of the instrument.

Handle 14A is provided with a slot 54 which accepts the rotatable knob 52. In addition, a polygonal shaped boss structure 57 is provided in the handle which will accept the corresponding polygonal shape of bushing member 56 when the instrument is constructed. The cooperation between structure 57 and bushing 56 allows for the incremental rotation of the body portion 18, and consequently the tool mechanism 28 to position the tool mechanism at various points along the rotational path. The number of faces presented by boss structure 57 is equivalent to the number of faces on the polygonal cross-section of bushing 56. Preferably, each structure has 12 faces.

In addition, FIG. 5 illustrates the preferred location of the electrical port 60, that being at the top of handle member 14A positioned at an angle to the longitudinal axis of the instrument formed by the body portion 18. Port 60 is preferably positioned at an angle of less than 30° to the longitudinal axis, and in its most optimal position, is positioned at 9° to the longitudinal axis. This affords the surgeon a clear line of sight down the longitudinal axis of the instrument to view the procedure at the surgical site. Port 60 accepts an electrical jack member through hole 61, and an electrical connection is made through the provision of a leaf spring member held in track 62 which connects the jack (not shown) with the outer tube member as seen at 63.

Figure 11A:
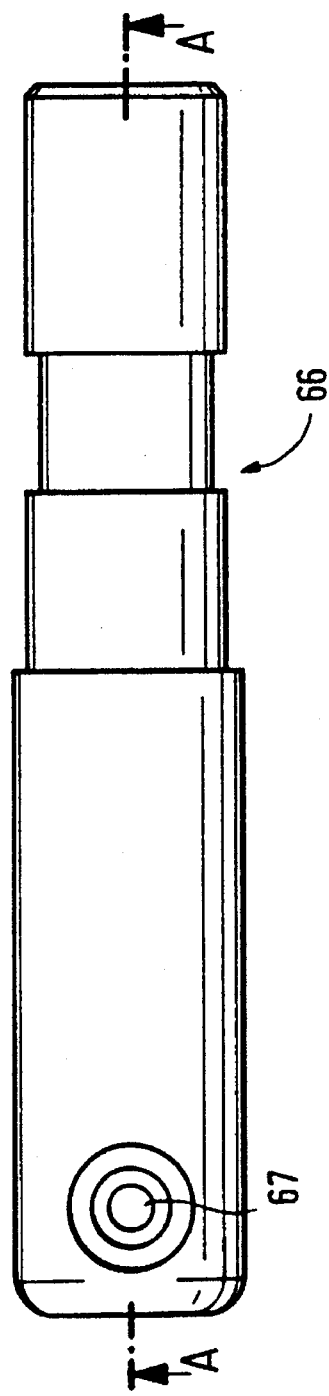
FIG. 11A illustrates a side view of a housing member of an endoscopic surgical instrument according to the present invention.
Figure 11B:
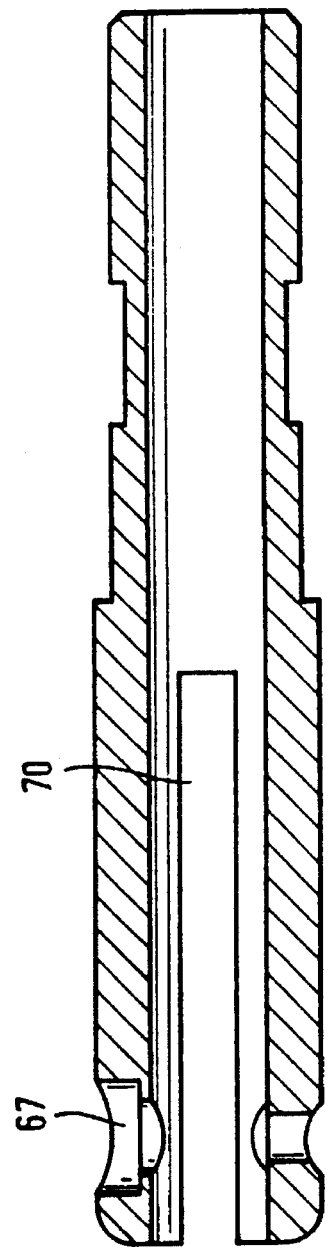
FIG. 11B illustrates a top cutaway view along lines A—A of FIG. 11A of a housing member of an endoscopic surgical instrument according to the present invention.

FIGS. 6A and 6B illustrate the tool mechanism which consists of, for example, a scissor mechanism including scissor blades 72 and 74. In this embodiment, a housing member 66 is attached to outer tube 20, and the tool mechanism is attached to housing member 66. Housing member 66 is shown in detail in FIGS. 11A and 11B, in which a diametric radial hole 67 is provided to accept pivot pin 68 to allow the tool mechanism to pivot about pin 68 during opening and closing. Housing member 66 is provided with a longitudinal slot 70 which allows the jaw members which comprise the tool mechanism to open and close, as best seen in FIGS. 11A and 11B.

As also shown in FIG. 6A, stiffening members 75 may be provided on scissor blades 72 and 74 which reinforce the blades and add strength to the blades. Stiffening members 75 allow for a very thin construction for blades 72 and 74, particularly at the distal end 77. Stiffening members 75 may comprise a detent or outwardly punched region whose addition to blades 72 and 74 bias the blades towards each other to enhance the shearing function of the blades. As the blades are made thinner, the resiliency of the blade material, preferably stainless steel, titanium, or a like metal, tends to decrease, and the provision of stiffening members 75 urges the blades 72 and 74 toward each other to maintain the efficiency of the cutting action. It is also contemplated that stiffening members 75 may comprise a built up region of material, or a layer of material fastened to the blades by adhesives, solder, or the like.

As best seen in FIG. 6B, scissor blades 72 and 74 are shown in the open position whereby the handle members (not shown) are in the open position, i.e., pivoting handle 16 is moved away from stationary handle 14.

As the handles move, inner rod member 22 slides through outer tube 20 towards jaw mechanism 28. As seen in FIG. 6B, scissor blades 72 and 74 are provided with cam slots 76 and 78, which slots accept a bearing post 80 which is attached to inner rod 22. As rod 22 moves, bearing post 80 slides within cam slots 76 and 78 to pivot blades 72 and 74 about stationary pivot point 68 to open and close the blades. When the blades open, the tail end of the blades pass through slot 70 in housing member 66 to allow the blades to open.

When handle members 14 and 16 are drawn towards each other, inner rod 22 slides away from the jaw mechanism and draws bearing post 80 towards the handle assembly. As this occurs, bearing post 80 slides in cam slots 76 and 78 to draw the blades closed.

Figure 6C:
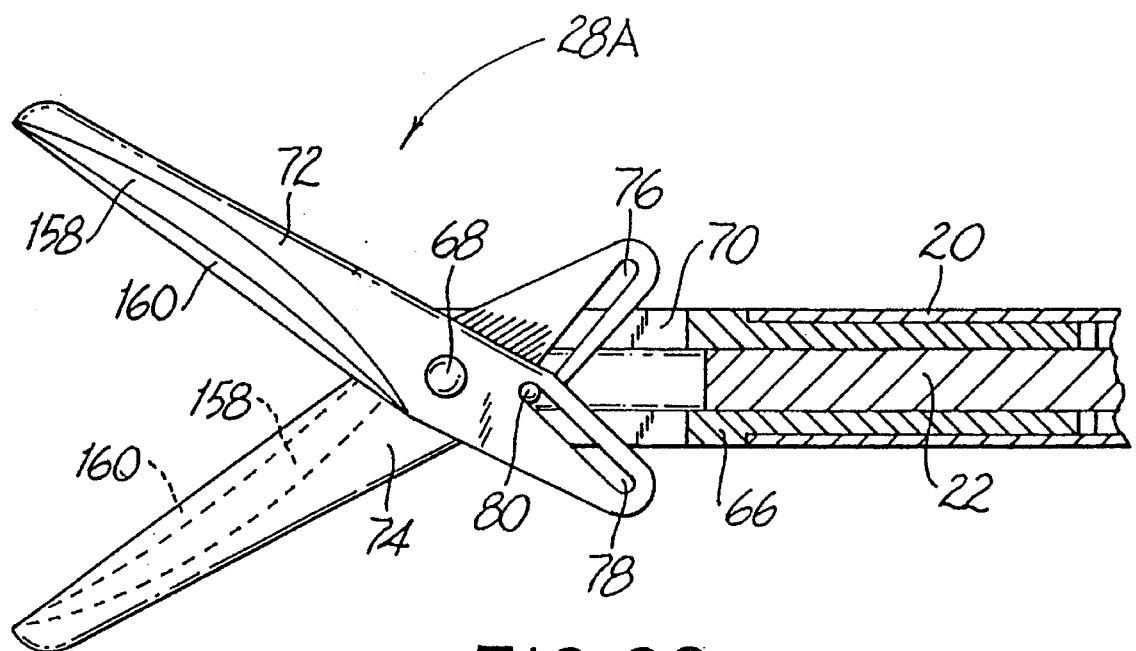
FIG. 6C illustrates a side cutaway view of the tool mechanism of another embodiment of an endoscopic surgical instrument according to the present invention.

Another embodiment of the endoscopic surgical instrument 10 is shown in FIG. 6C. The endoscopic surgical instrument includes a tool mechanism 28A having scissor blades as in the previous embodiment shown in FIGS. 6A and 6B. However, in the embodiment shown in FIG. 6C, each scissor blade 72, 74 includes a blade edge 158 and an inflected surface 160 which is directed away from the outer surface of the blade and towards the opposite blade. In typical surgical cutting instruments, when the reciprocating blades are in a closed position a gap may exist between the blades. Endoscopic surgical procedures require precision cutting action and superior cutting ability. The inflected surfaces 160 substantially contact continuously along the blade edge 158 when the scissor blades 72, 74 are in mutual cooperation, thereby eliminating any gap between the blade surfaces.

It is understood that the endoscopic surgical device as described above and illustrated in FIG. 6C, may include an inflected surface 160 on only one cooperating scissor blade. The scissor blades 72, 74 communicate in the same fashion as described above.

Preferably, the inflected surface 160 may be manufactured, for example, by rolling or grinding a portion of the blade edge 158 after the blade edge 158 is cut or stamped from, for example, steel. A metal harder than the steel fabricated blades, such as, for example, carbide steel is used to roll or grind the inflected surface.

The inflected surface 160 preferably may be, for example, at an acute angle to a vertical plane in which the blade edge 158 lies. The acute angle, for example, preferably may be between 40 degrees and 50 degrees. Moreover, the acute angle, for example, most preferably may be 45 degrees.

Further, the inflected surface 160 preferably may extend, for example, between 0.0009 inches and 0.003 inches from the blade edge at a desired angle. Moreover, the inflected surface 160 most preferably may extend, for example, between 0.001 and 0.002 inches from the blade edge at a desired angle.

Figure 7:
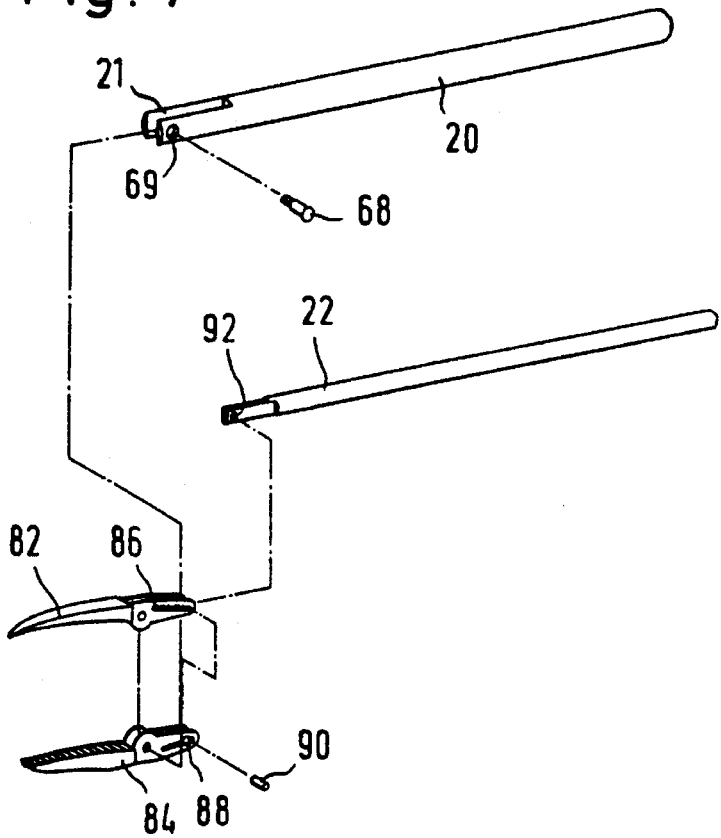
FIG. 7 illustrates an exploded perspective view of an alternate tool mechanism of an endoscopic surgical instrument according to the present invention.

Turning to FIG. 7, FIG. 7 illustrates an exploded perspective view of a dissector device which may comprise tool mechanism 28. In this embodiment, outer tube 20 is provided with a slot 21 which allows for the opening and closing of the dissector members. In this embodiment, housing member 66 is eliminated.

The dissector members 82 and 84 are provided with a cam slot arrangement similar to the device illustrated in FIG. 6B. Cam slot 86 is provided on upper dissector member 82, and cam slot 88 is provided on lower dissector member 84. In this embodiment, inner rod 22 is positioned within outer tube 20, while dissector members 82 and 84 are pivotally secured to outer tube 20 by means of pivot pin 68 which passes through hole 69 in tube 20. Rod 22 is secured to the cam slot arrangement through the provision of bearing post member 90. As rod member 22 is slid forward within tube 20, bearing post 90 slides in cam slots 86 and 88 to pivot the dissector members about pivot point 68 to open the members, and when the rod member 22 is slid away from the dissector mechanism, post 90 slides in cam slots 86 and 88 away from the dissector mechanism to draw the dissector members 82 and 84 into a closed position, as best seen in FIG. 9.

Figure 9:
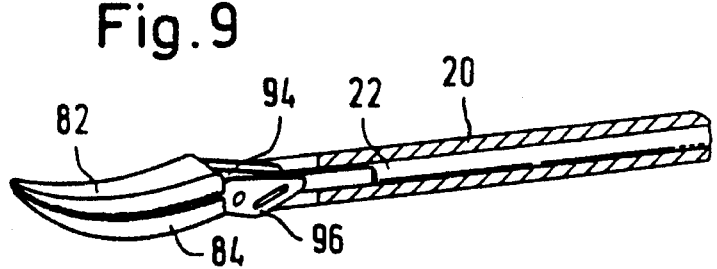
FIG. 9 illustrates a partial cutaway side view of the dissector mechanism of FIGS. 8A and 8B attached to the end of an endoscopic surgical instrument according to the present invention.

As also seen in FIG. 9, as the jaws close, the distal tips of the jaw members 82 and 84 contact each other before the ends nearest the pivot point contact each other. An angle of less than 6° is maintained at this point, and preferably 2°, to allow for progressive application of pressure at the jaws.

Figure 8A:
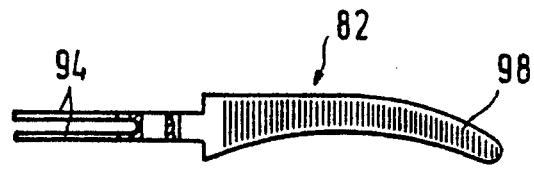
FIG. 8A illustrates a plan view of the upper member of a dissector mechanism for use with an endoscopic surgical instrument according to the present invention.
Figure 8B:
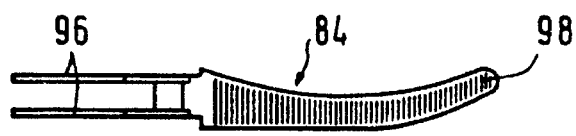
FIG. 8B illustrates a plan view of a bottom member of a dissector mechanism for use with an endoscopic surgical instrument according to the present invention.

FIGS. 8A and 8B illustrate the preferred embodiment of the dissector device, in which the body portion has a crescent shape to facilitate grasping and tearing tissue. The surface of the dissector members include serrations 98 which are provided for dissecting and tearing tissue during a surgical procedure. Overlapping projections 94 and 96, on which cam slots 86 and 88 are formed, allow the dissector mechanism to open and close without interfering with each other. The spacing between projections 94 is less than the spacing between projections 96, such that projections 94 fit within projections 96. Slot 21 is provided on outer tube 20 allow the projections to pass outside the perimeter of tube 20 to allow the dissector mechanism to open and close.

Figure 10A:
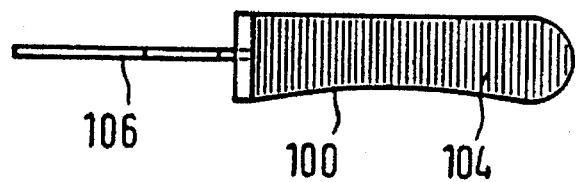
FIG. 10A illustrates a plan view of an upper member of a molded plastic grasper mechanism.
Figure 10B:
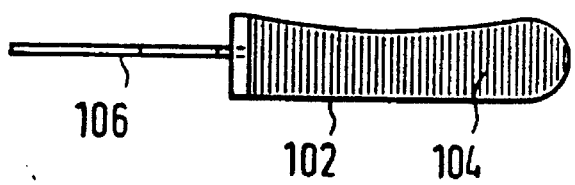
FIG. 10B illustrates a plan view of a bottom member of a molded plastic grasper mechanism.
Figure 10C:
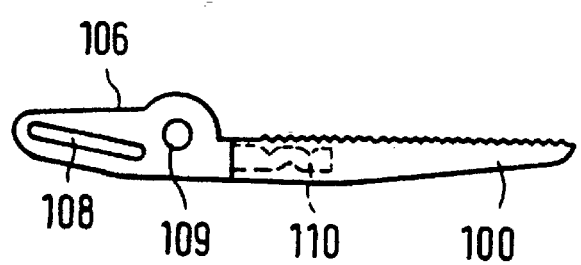
FIG. 10C illustrates a side view of a member of a grasper mechanism.

FIGS. 10A through 10E illustrate a grasping mechanism which may be used as the tool mechanism on the endoscopic surgical instrument of the present invention. FIGS. 10A and 10B illustrate a cooperating pair of grasping members 100 and 102 which are provided with serrations 104 to facilitate the grasping and holding of tissue. In the embodiment shown in FIGS. 10A and 10B, the body portions 100 and 102 are preferably constructed of a plastic material which is integrally molded about projection 106. As best seen in FIG. 10C, a post member 110 is provided about which the members 100 and 102 are molded. Projection 106 is provided with cam slot 108 and pivot hole 109 so that the grasping mechanism may be operated in a manner similar to that previously described above in connection with the scissor mechanism and the dissector mechanism.

Figure 10D:
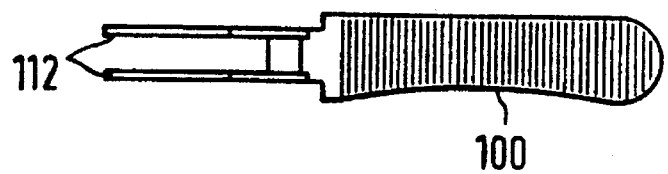
FIG. 10D illustrates a plan view of an upper grasper member constructed of metal.
Figure 10E:
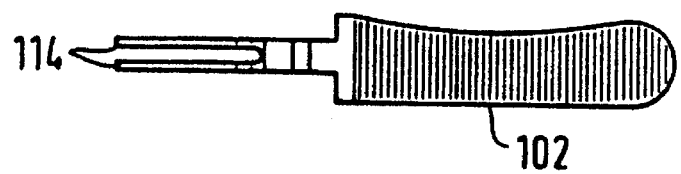
FIG. 10E illustrates a plan view of a bottom member of a grasper mechanism constructed of metal.

FIGS. 10D and 10E illustrate the grasping mechanism of FIGS. 10A through 10C except where the entire mechanism is constructed of metal, such as stainless steel, titanium, cast aluminum or the like. Projections 112 and 114 cooperate in a manner similar to that described above for the dissector device, where projections 112 are spaced greater than the distance between the projections 114 so that projections 114 may pass between projections 112 during opening and closing of the grasping device.

Figure 12A:
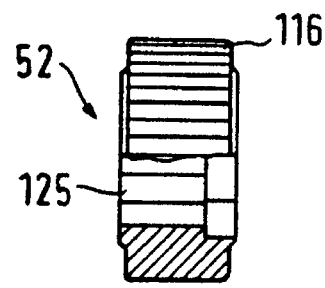
FIG. 12A illustrates a side partial cutaway view of a rotator knob for use in an endoscopic surgical instrument of the present invention.
Figure 12B:
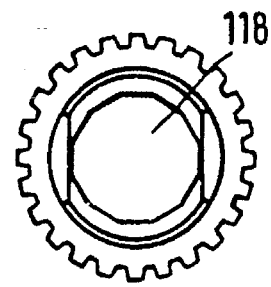
FIG. 12B illustrates a front view of the rotatable knob of FIG. 12A.
Figure 13A:
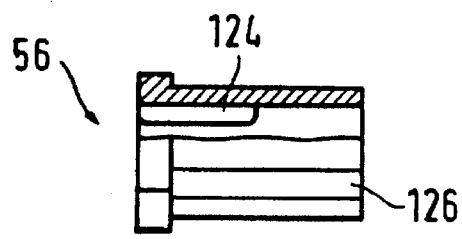
FIG. 13A illustrates a side partial cutaway view of a bushing member for use in an endoscopic surgical instrument according to the present invention.
Figure 13B:
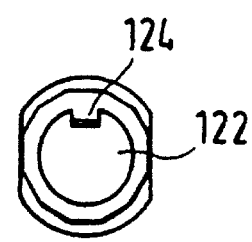
FIG. 13B illustrates a front view of the bushing of FIG. 13A.

Turning now to FIGS. 12 and 13, there is illustrated the rotatable knob 52 and bushing member 56 which are used in connection with the rotatable body portion to rotate the body portion and tool mechanism. Rotatable knob 52 is preferably knurled or provided with ridges 116 to allow for easy manipulation by the surgeon's thumb or fingers. Rotatable knob 52 is preferably hollow and includes a passageway 118 to allow the bushing member 56 to pass therethrough. FIG. 13A illustrates the bushing member as having a polygonal cross-section, such that it is provided with a series of faces 126 which cooperate with faces 125 on the rotatable bushing. The bushing extends outwardly from rotatable knob 52 (see FIG. 4), and faces 126 cooperate with boss structure 57 (see FIG. 5) to provide for incremental rotation of the body portion 18 to position the tool mechanism at various points along the rotational axis. FIG. 13B best illustrates boss member 124 which allows for connection and securement of the bushing to outer tube 20. Boss 124 fits into a groove or slot in tube 20 to secure the bushing and rotatable knob to outer tube 20. It is also contemplated that bushing 56 and rotatable knob 52 are constructed as a single integral unit. Knob 52 and bushing 56 are preferably constructed of plastic, so that insulation is provided during use of the electrocautery feature.

The positioning of the rotatable knob on the stationary handle allows the surgeon to use the endoscopic surgical instrument 10B with one hand, so that as the surgeon is holding the device he may rotate the knob with his thumb while keeping his other hand free to control the surgical procedure.

Figure 14A:
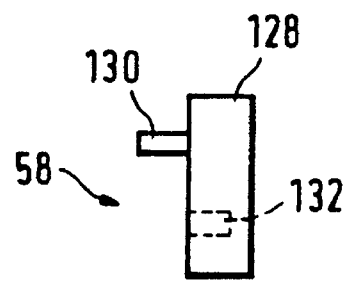
FIG. 14A illustrates a side view of a pivot bushing for use with an endoscopic surgical instrument according to the present invention.
Figure 14B:
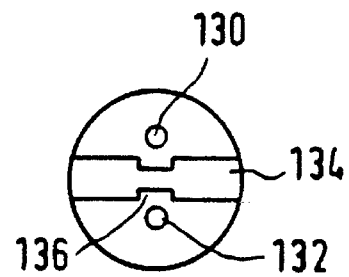
FIG. 14B illustrates a front view of the pivot bushing of FIG. 14A.

As the knob is rotated, the outer tube is rotated which in turn rotates pivot point 68, which consequently rotates the tool mechanism. Rotation of the tool mechanism causes rotation of the inner rod 22, which is accomplished within pivot bushing 58. Pivot bushing 58 is best illustrated in FIGS. 14A and 14B and comprises a pair of discs 128 each having a post member 130 and a hole 132 formed therein for interengaging the discs with each other. Groove 134 is provided with a notch portion 136 which accepts the end of rod member 22 which is formed with a corresponding notch. This notch secures rod 22 in place for longitudinal movement, while at the same time allowing for rotational movement. As stated above, as handle member 16 pivots, bushing 58 rotates to greatly reduce or eliminate radial deflection of the rod member within the tube. This alleviates the torquing forces on the rod and minimizes damage to the device after extended use.

Figure 15:
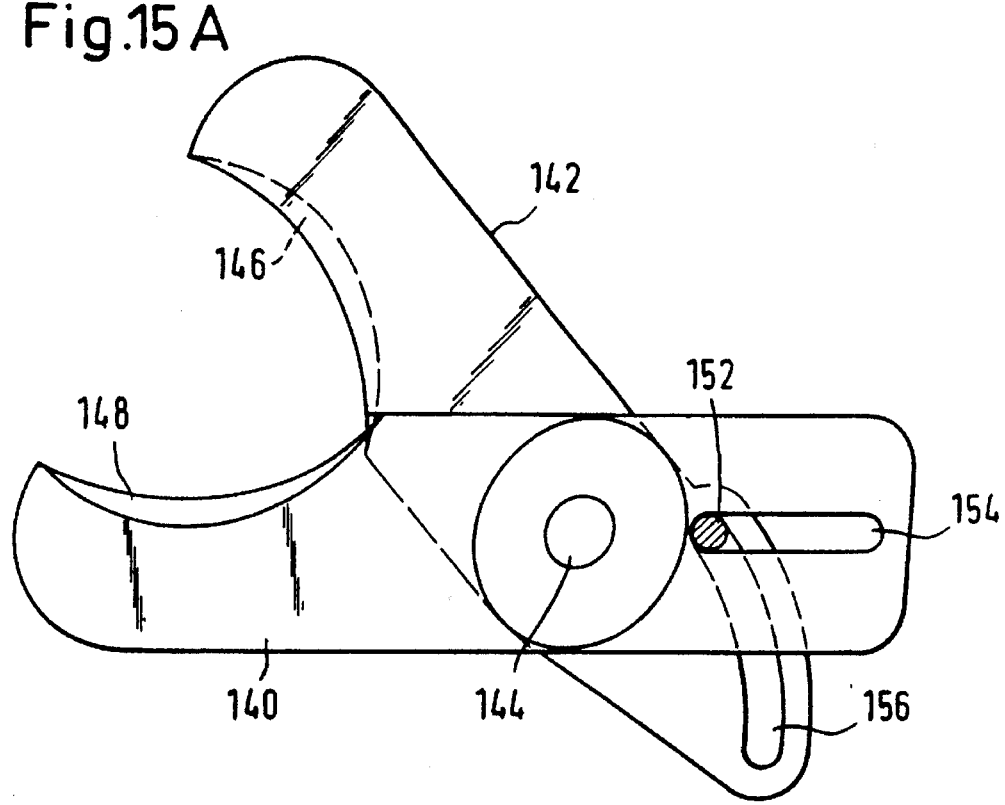
FIG. 15A illustrates a side view of an open scissor mechanism in accordance with the present invention wherein only one jaw member pivots.
FIG. 15B illustrates a side view of the scissor mechanism of FIG. 15A in the closed position.
FIG. 15C illustrates a top view in cross-section of the stationary pivot pin of the scissors in FIG. 15A and 15B.
Figure 15:
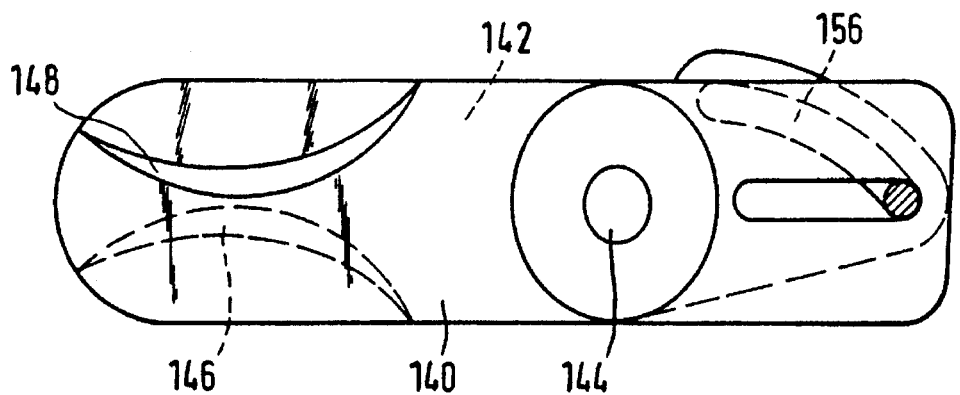
Figure 15:
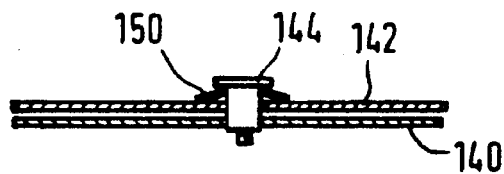
Figure 16:
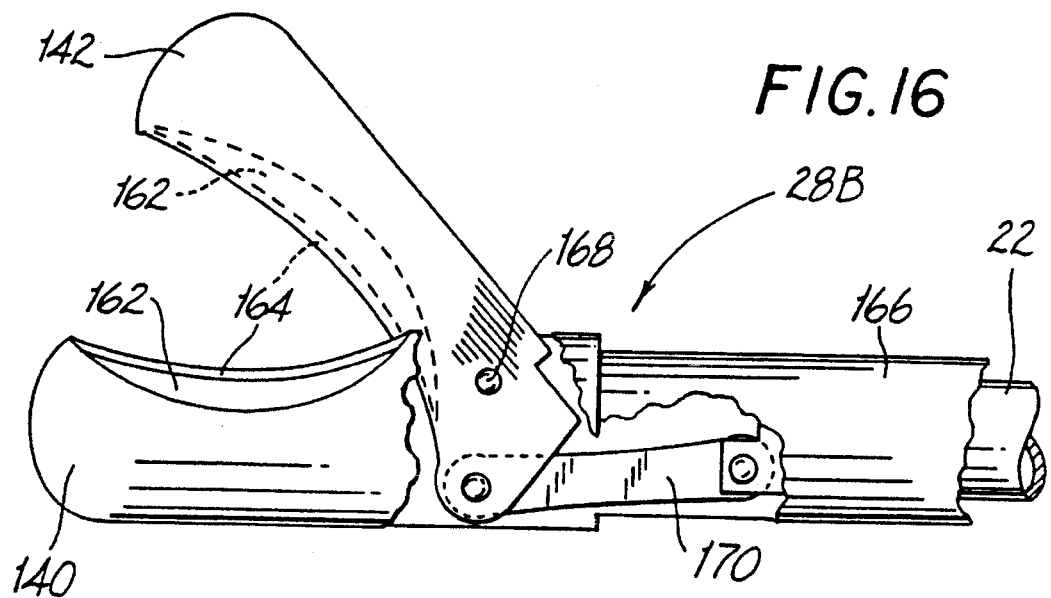
FIG. 16 illustrates a side view of a tool mechanism with blade members in an open position of another embodiment according to the present invention.

FIGS. 15A and 15B illustrate a further embodiment of the tool mechanism in accordance with the present invention.

Stationary scissors blade 140 is attached to movable scissors blade 142 about transverse stationary pivot pin 144. This transverse pin 144 is attached to housing member 66 through radial hole 67 as discussed above (see FIGS. 11A and 11B). The present scissors embodiment utilizes a shearing motion of blades 140 and 142 in order to separate tissue. Arcuate cutting surfaces, 146 and 148 respectively, are formed on opposed vertical faces of the distal ends of blades 140 and 142 to better facilitate the shearing cutting action. In a particularly advantageous embodiment, a spring washer 150, see FIG. 15C, is provided to urge movable blade 142 against stationary blade 140. The urging force providing a better cutting action as the blades 40 and 142 shear against each other.

A transverse bearing post 152 is attached to inner rod 22 and adapted for reciprocal longitudinal motion within outer tube 20. A longitudinal slot 154 is provided in a proximal end of stationary blade 140 in an area proximal to and in longitudinal alignment with transverse pivot pin 144. Bearing post 152 interfits with slot 154 for longitudinal motion therein and serves to prevent pivotal motion of blade 140 about pivot pin 144.

An arcuate cam slot 156 is provided in a proximal end of movable blade 142 in an area proximal to transverse pivot pin 144. Bearing post 152 interfits within arcuate cam slot 156 and serves to translate the longitudinal motion of inner rod 22 relative to outer tube 20 into pivotal motion of blade 142 about pivot pin 144. Thus, in the embodiment shown in FIGS. 15A and 15B, as transverse bear post 152 moves distally from its proximal position, blade 142 is cammed open relative to blade 140 which remains in the same longitudinal plane as rod 22. Correspondingly, proximal motion of rod 22 causes bear post 152 to cam blade 42 to a closed position as shown in FIG. 15B.

This embodiment is directed to a shearing scissors mechanism, however, other mechanisms such as, for example, graspers, dissectors, clamps etc. are contemplated.

Another embodiment of the endoscopic surgical instrument 10 is shown in FIGS. 16-23. The endoscopic surgical instrument 10 includes a tool mechanism 28B having a stationary blade 140 and a movable blade 142 cooperating with a handle assembly 12 by an inner rod member 22 as in the previous embodiment shown in FIGS. 15a and 15b. Similarly, the blades 140, 142 each have arcuate shaped cutting surfaces 162. However, in the embodiment of the endoscopic surgical instrument shown in FIGS. 16–23, preferably, the stationary blade portion 140 is integral with a housing assembly 166. Further, both blades 140, 142 include a blade edge 162 and an inflected surface 164. As in the previous embodiment illustrated in FIG. 6C, the inflected surfaces 160 eliminate a gap between the blades 140, 142 when the blades are in a closed position.

Figure 17:
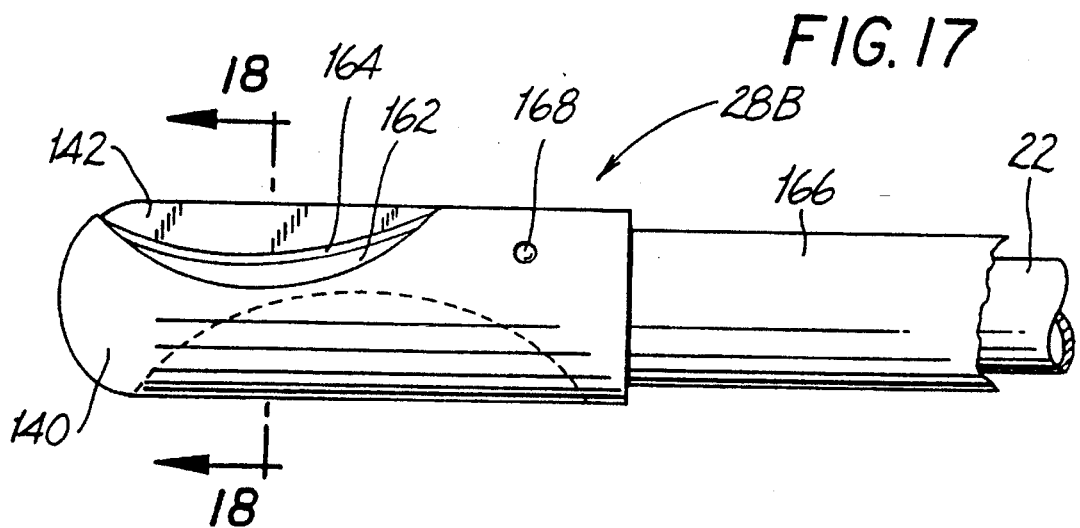
FIG. 17 illustrates a side view of the tool mechanism shown in FIG. 16 with the blade members in a closed position according to the present invention.

Referring to FIG. 17, the stationary blade portion 140 and the housing assembly 166 of the endoscopic surgical instrument 10 is shown having the blades 140, 142 in a closed position. The inflected surfaces 160 of the blades 140, 142 cooperate to substantially eliminate any gap between the blades 140, 142 when the blades are in a closed position.

Figure 18:
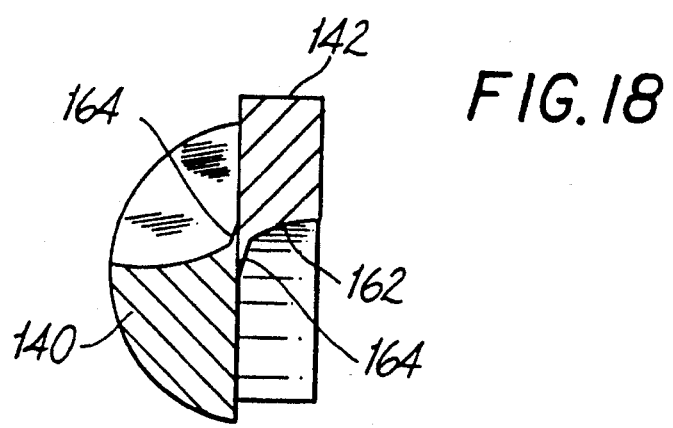
FIG. 18 illustrates a cross-sectional view of the tool mechanism shown in FIG. 17 taken along line 18—18.

As shown in FIG. 18, the inflected surfaces 164 substantially close any existing gap between the blades 140, 142. The gap between blades without the inflected surface 164 is typically, for example, between 0.001 inches to 0.003. This is disadvantageous because a surgeon, in some cases, may not be able to achieve the clinical results desired, and for example, ripping or tearing of tissue may occur. Preferably, both blade edges have an inflected surface 164 directed towards each other that may be, for example, 0.001 inches to 0.002 inches toward the other blade.

The inflected surface 164 is preferably continuous along the blade edge 162, so that, the cooperation between the inflected surface 164 on the blades 140, 142 substantially closes the gap between the two blades, bringing the blades into substantial contact along the blade edge. The inflected surface 164 on the blade edge 162 allows precision cutting of a specimen. The endoscopic surgical instrument 10 thereby, allows a surgeon to achieve critical tolerances desired when performing certain surgical procedures.

The housing assembly 166 of the endoscopic surgical instrument 10 includes a pivot point 168 which allows the movable blade 142 to pivot in cooperation with the stationary blade 140. The pivot point 168 preferably is offset from a horizontal diametric line in reference to the housing 166. It is understood that the pivot point 168 may also be positioned substantially about the horizontal diametric line. The movable blade 142 is attached to the rod member 170 at its proximal end. The rod member 170 pivots the movable blade 142 about the pivot point 168 in response to employment of the handle assembly 12. The movable blade portion also includes an abutment portion at its proximal end, as described below.

Figure 19:
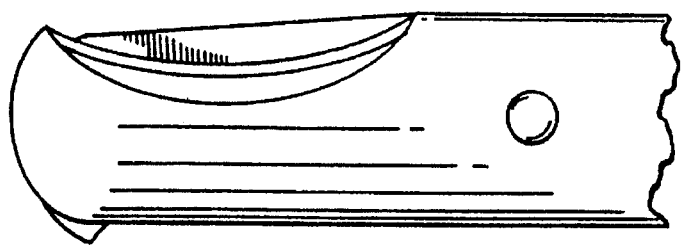
FIG. 19 illustrates a side view of a tool mechanism of a prior art endoscopic surgical instrument.

As shown in FIGS. 16–19 the endoscopic surgical instrument 10 preferably includes an abutment surface 174 at its upper proximal region for preventing the blade members 140, 142 from becoming overstroked. Referring to FIG. 19, there is illustrated blade members of an endoscopic surgical instrument which are overstroked. Overstroke occurs when one pivoting blade or both pivoting blades rotate past a desired closed position. As illustrated in FIG. 19 the blade has rotated past the closed position such that the point where the maximum amount of blade surface contacts is surpassed.

Figure 20:
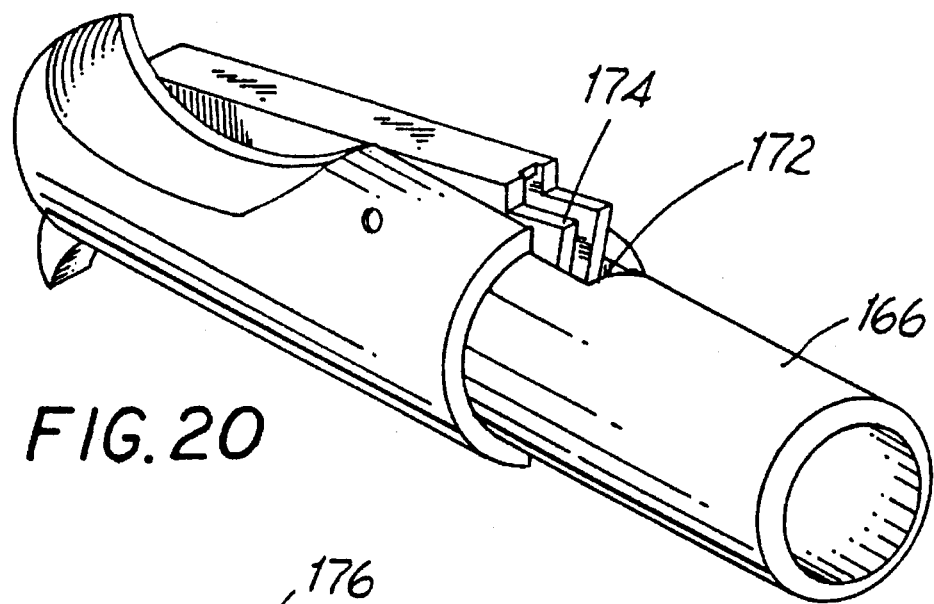
FIG. 20 illustrates a perspective view of the tool mechanism of an endoscopic surgical instrument according to the present invention.

As shown in FIG. 20, the housing assembly 166 of the endoscopic surgical instrument 10 of the present invention includes a longitudinal slot 172 substantially along a center line allowing the abutment surface 174 to protrude from the housing assembly 166.

Figure 21:
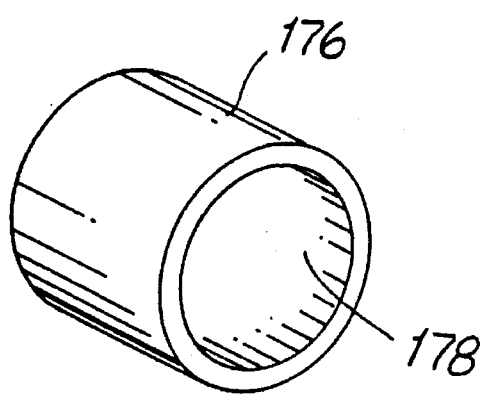
FIG. 21 illustrates a perspective view of a sleeve portion for use with an endoscopic surgical instrument according to the present invention.
Figure 22:
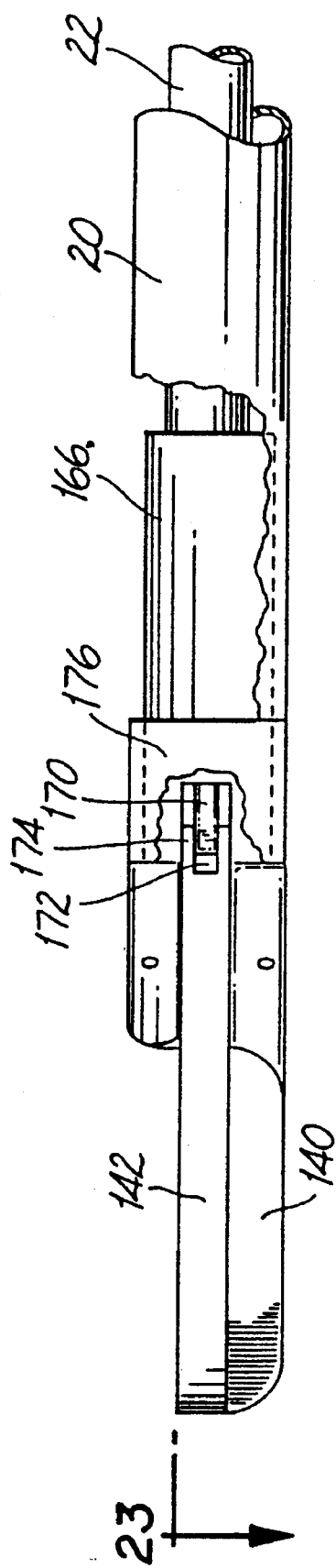
FIG. 22 illustrates a plan view of the tool mechanism of an endoscopic surgical instrument according to the present invention.
Figure 23:
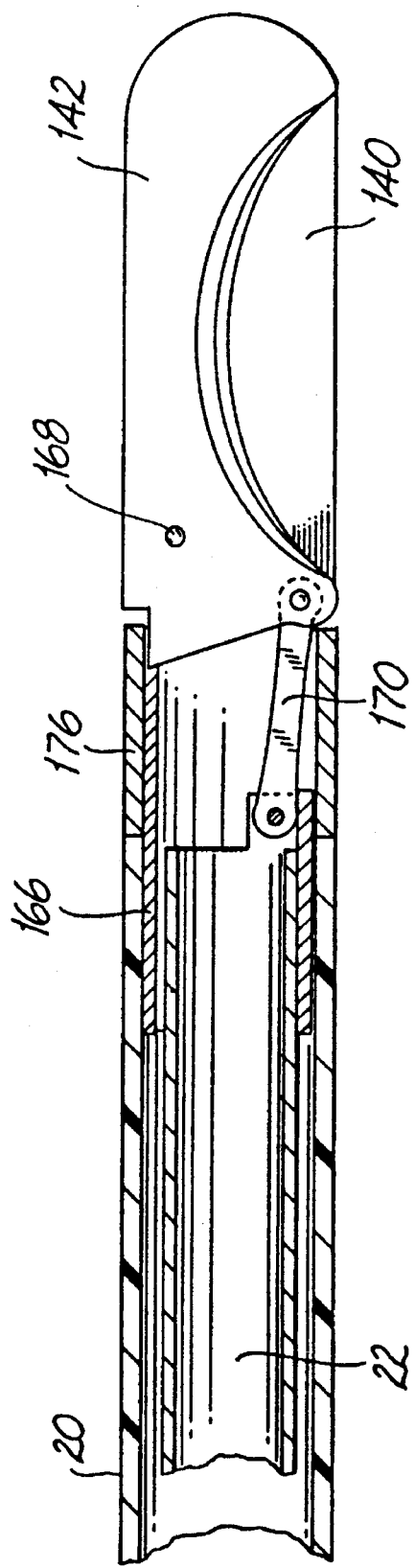
FIG. 23 illustrates a side view of the tool mechanism of an endoscopic surgical instrument according to the present invention.

As shown in FIGS. 21, 22 and 23 a sleeve portion 176 is placed about the housing assembly 166 and is continuous with the outer tube 20. The abutment surface 174 strikes the inner face 178 of the sleeve portion 176 to prevent the blades 140, 142 from becoming overstroked. The rotating blade 142 pivots about the pivot point 168 to a desired closed position. At that position the abutment surface 174 at its proximal end communicates with the inner face 178 of the sleeve portion 176 by proceeding through the longitudinal slot 172 in the housing assembly 166, as shown in FIGS. 22 and 23.

The sleeve portion 176 is preferably of a material stronger than the outer tube 20, thus, making the sleeve portion 176 reinforced. The sleeve portion 176 may be, preferably, of steel and can withstand repeated strikes from the abutment surface 174 without deforming.

Typically, blade members may tend to separate when, for example, an endoscopic surgical instrument is used to dissect hard substances or opened and closed repeatedly. Because of the forces precipitated by the substances encountered, the blades may tend to move apart or splay from each other such that a gap between the blades becomes evident, or an existing gap increases.

To discourage splaying of the blades, the sleeve portion 176 may further be used for preventing the blade members 140, 142 from separating, as well as its use described above for receiving the abutment surface 174. In use, the sleeve portion 176 surrounds the housing assembly 166 such that the movable and stationary blades 142, 140 are coerced towards each other. Thus, after repeated uses of the endoscopic surgical instrument 10 on hard substances the blades 140, 142 are discouraged from splaying by the sleeve portion 176.

Typically, the endoscopic surgical instrument 10 outer tube 20 is for example, of aluminum. Aluminum is typically insufficiently strong to prevent splaying of the blades. Preferably, therefore, the sleeve portion 176 may be made of steel, so that the sleeve portion 176 is sufficiently strong to inhibit movement of the blades 140, 142 apart from each other.

Figure 24:
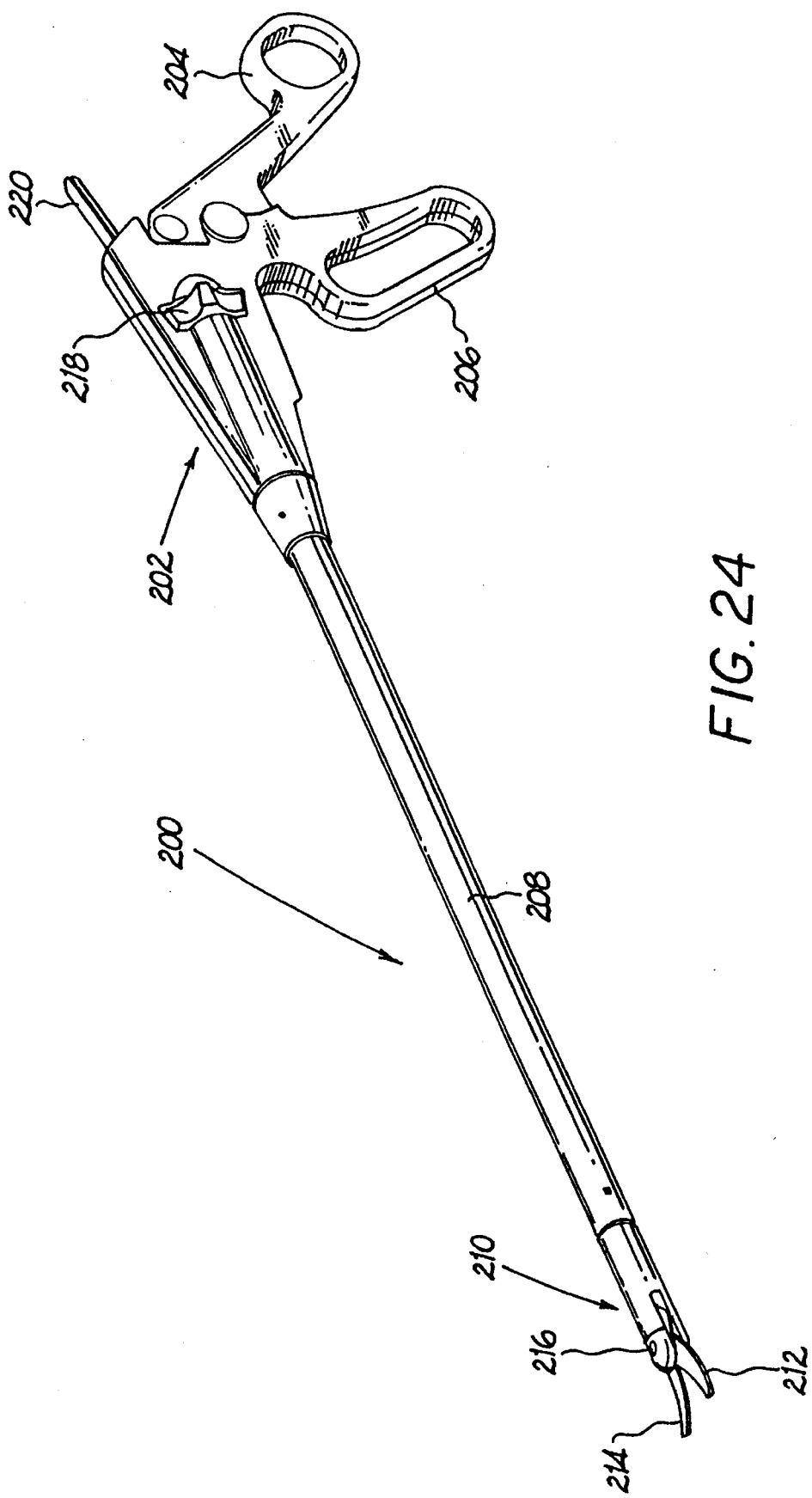
FIG. 24 illustrates a perspective view of an alternate embodiment of an endoscopic surgical cutting instrument of the present invention.
Figure 25:
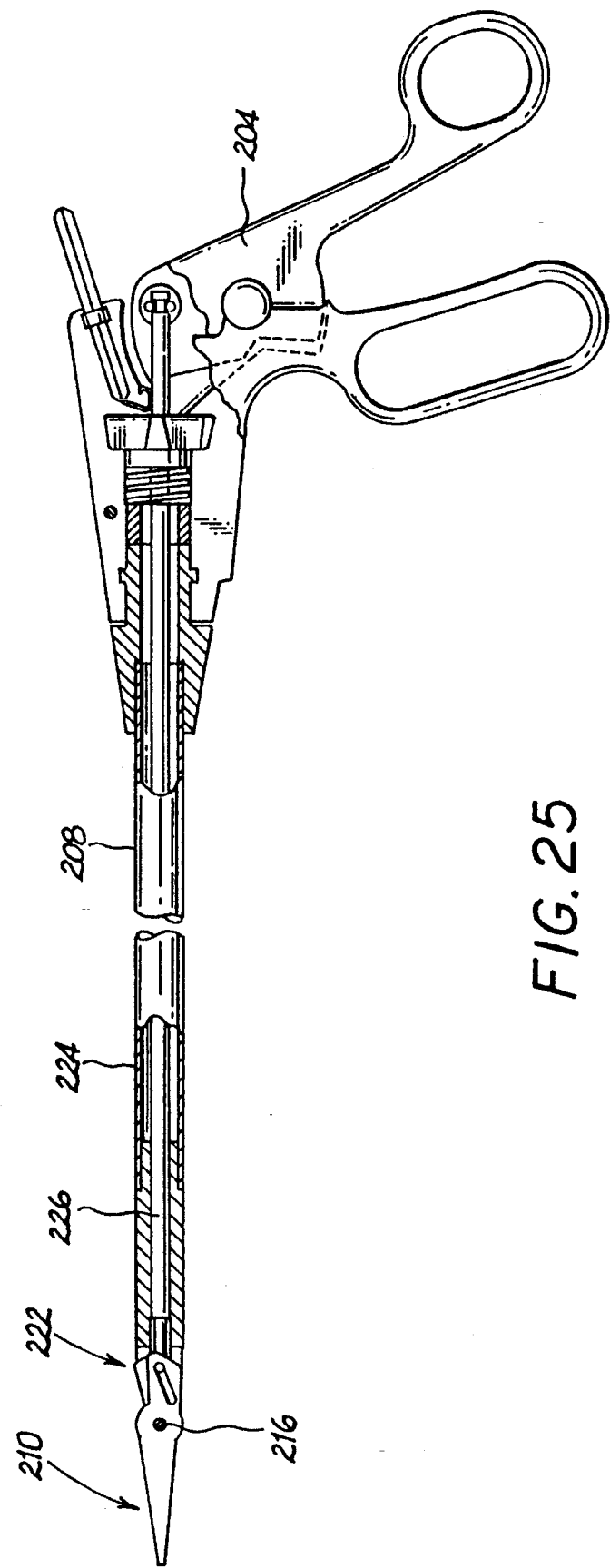
FIG. 25 illustrates a side partial cut away plan view of the instrument of FIG. 24.

A further embodiment of the present invention is illustrated at FIG. 24. Endoscopic surgical cutting instrument 200 is similar to the surgical instruments disclosed above except for the novel cutting mechanism 210 positioned at the distal end of the elongated body portion 208. Instrument 200 further includes handle assembly 202 which is comprised of pivoting handle 204 and stationary handle 206. As best seen in FIG. 25, body portion 208 includes outer tube member 224 and inner rod member 226 which function as described above. Inner rod 226 moves in response to movement of pivoting handle 204. Body portion 208 terminates in cutting mechanism 210 which essentially is comprised of blade member 212 and blade member 214 secured at a distal end of body portion 208 at pivot point 216. Blade members 212 and 214 pivot about pivot point 216 in response to movement of pivoting handle 204. The pivoting handle 204 reciprocatingly moves inner rod member 226 to open and close cutting mechanism 210 through the provision of linkage mechanism 222. The operation of instrument 200 is identical to that described above. As also described above, handle assembly 202 may include rotatable knob 218 to selectively position cutting mechanism 210 at any orientation about the longitudinal axis of the instrument. Handle 202 may also include provisions for electrocautery procedures through pin 220.

Figure 26A:
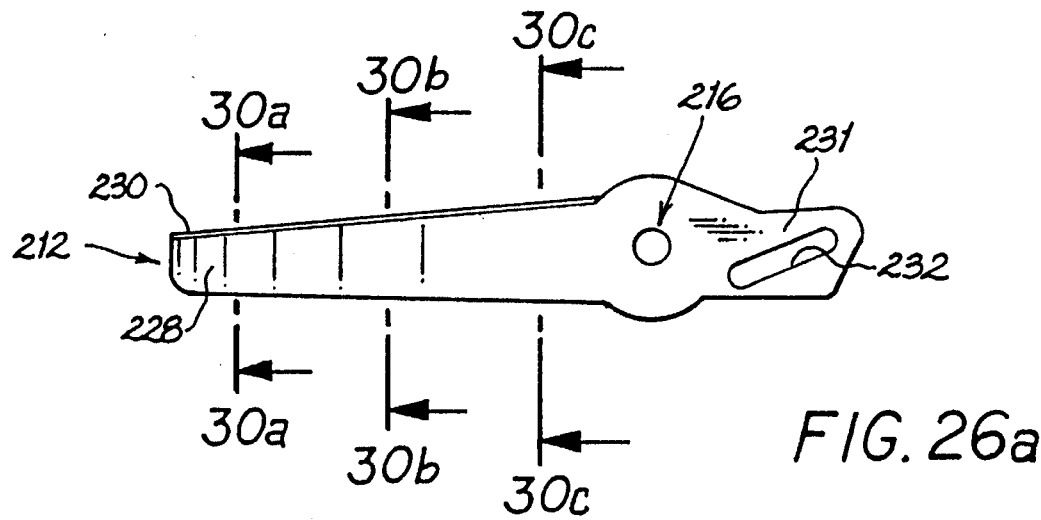
FIGS. 26A and 26B illustrate a side plan view and top plan view, respectively, of one of the blade members of the cutting instrument of the present invention.
Figure 26B:
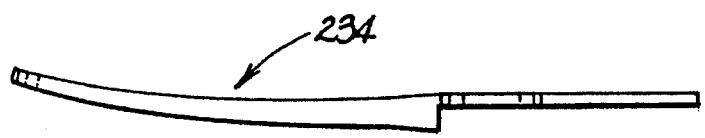
Figure 27A:
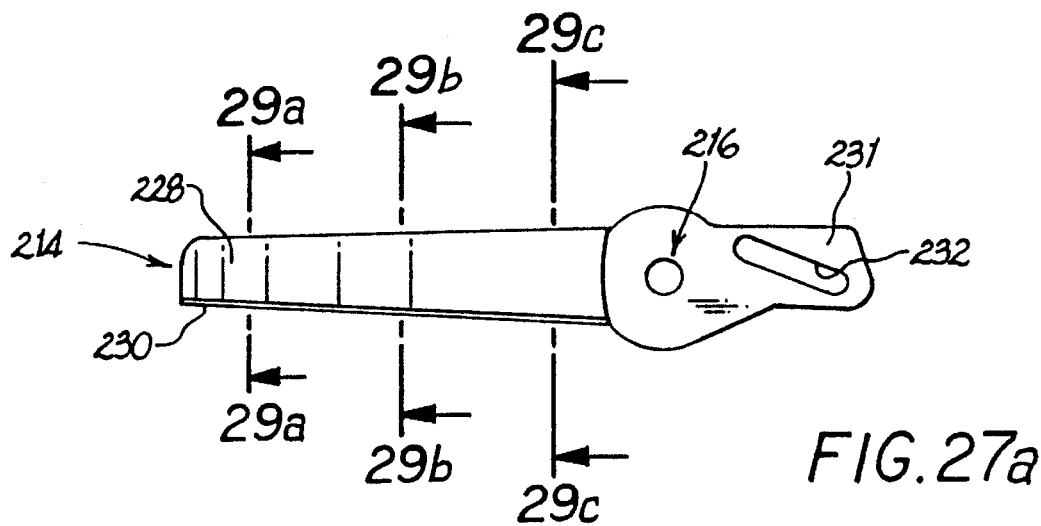
FIGS. 27A and 27B illustrate a side plan view and a top plan view, respectively, of a second blade member of the cutting mechanism of the present invention.
Figure 27B:
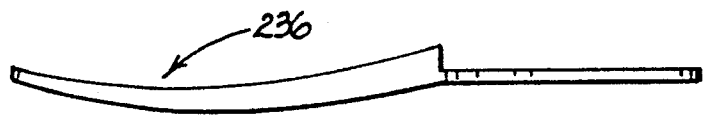

Turning now to FIGS. 26 and 27, there is illustrated the blade members 212 and 214 of cutting mechanism 210. FIGS. 26A and 26B illustrate a first blade member 212, which for purposes of clarity may be considered the "bottom" blade. FIGS. 27A and 27B illustrate blade member 214, which again for purposes of this discussion, may be considered the "top" blade member. As seen in FIG. 26A, blade member 212 includes blade portion 228 having a cutting edge 230 applied thereon during a grinding operation. The blade member itself is preferably metal injection molded to be crescent shaped as seen in FIG. 26B. Blade member 212 further includes camming portion 231 which is part of the linkage mechanism 222 described above. Camming slot 232 is provided which functions identical to that described above in relation to FIGS. 6A through 6C, and a hole is provided to accommodate pivot point 216 as shown.

FIG. 27A illustrates the top blade member 214, which is similar in construction to bottom blade member 212. The radius of curvature at surface 236 of top blade member 214 is the same as the radius of curvature of bottom blade member 212 at surface 234. Surfaces 234 and 236 represent the cutting surfaces of the blade members which face each other when the cutting mechanism is assembled. After assembly, however, the radius of curvature of blade member 214 is different than the radius of curvature of blade member 212 relative to pivot point 216, such that the radii of curvature are offset from each other. The different radii of curvature relative to the pivot point 216 provides a cutting mechanism in which the blades contact each other during opening and closing at a single point and include a gap 244 between the blade members that "follows" the contact point 246 during closing. (See FIG. 31)

Referring now to FIGS. 29 and 30, there is illustrated cross-sectional views of blade members 212 and 214 taken along various points of the length of blade portion 228. FIGS. 29A through 29C illustrate top blade 214 and show inside surface 240 which faces bottom blade 212. As seen in the figures, inside surface 236 is angled during the grinding of the blade member to apply cutting edge 230 to the blade member. The inside surface 236 is angled towards cutting edge 230 to define a relief angle Θ which is less than 5° and preferably between 2° and 3°. The relief angle enhances the shearing action of the blades by angling the cutting edges 230 towards each other. FIGS. 30A through 30C illustrate the relief angle Θ on inside surface 234 for the bottom blade 212.

Figure 31:
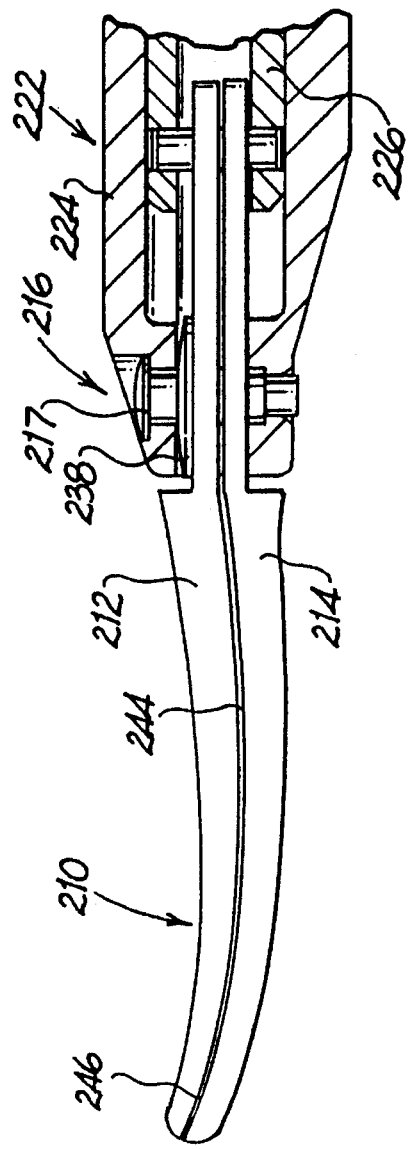
FIG. 31 illustrates a plan view in partial cross-section of the cutting mechanism of the instrument of FIG. 24 in the closed position.
Figure 32:
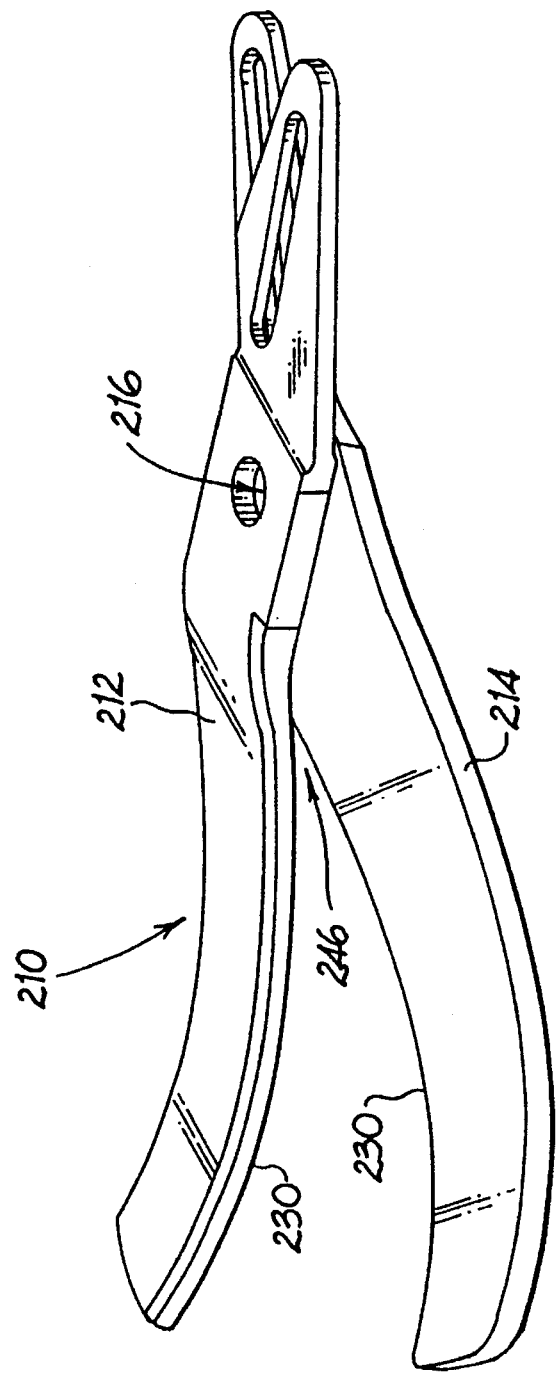
FIG. 32 illustrates a perspective view of the blade members in the open position.

FIGS. 31 and 32 illustrate the cutting mechanism 210 in an enlarged view, and the operation of cutting mechanism 210 will be described at this time. As seen in FIG. 31, cutting mechanism 210 is secured to outer tube 224 and pivots about pivot point 216, which essentially comprises a pin 217. Cutting mechanism 210 is operable to open and close in response to movement of inner rod 226 which engages cutting mechanism 210 through linkage mechanism 222. The opening and closing of the mechanism is identical to that described above.

Blade members 212 and 214 are metal injection molded into a crescent shape and during assembly are provided with different radii of curvature relative to pivot point 216 as best seen in FIG. 31. The radius of curvature of blade member 214 relative to pivot point 216 is offset from the radius of curvature of blade 212 and enhances the shearing action of the blade members during closing by providing for contact between the blade members at their cutting edge at a single point as the blade is closed. In the preferred embodiment, the radius of curvature of blade 212 is offset from the radius of curvature of blade 214 by approximately 0.032 inches, so that gap 244 is provided and which is measured to be approximately 0.020 inches. The illustration shown in FIG. 31 shows the blades completely closed, and shows single contact point 246 at the distal end of the blade members, while FIG. 32 shows the blade members 212 and 214 in the open position. Contact point 246 moves along the cutting edges 230 as the blade members are opened and closed. Due to the differing radii of curvature relative to the pivot point 216, gap 244 is provided between the blades which follows the single contact point 246 as the blades are opened and closed. Spring washer 238 provides additional means urging the blade members together to prevent separation of the blades in the event the tissue or stronger items such as staples or sutures are encountered.

As linkage mechanism 222 opens and closes the blade members, spring washer 238 urges the blades towards each other. The differing radii of curvature relative to the pivot point 216 causes the blades to contact at a single point 246 along the cutting edge 230. The relief angle causes the blade members to taper towards the cutting edge to further ensure contact between the blades at the cutting edge 230. The combination of the relief angle, the differing radii of curvature relative to the pivot point, the increased thickness of the blade members at the proximal end, and the spring washer 238 cooperate to enhance the cutting action of cutting mechanism 210 to shear tissue typically up to 0.035 inches in thickness. Cutting mechanism 210 also provides for the cutting of sutures and staples during the endoscopic surgical procedure, if necessary.

The endoscopic surgical instrument of the present invention is a compact, lightweight and easy to use instrument incorporating many features required during endoscopic surgical procedures which allows the surgeon to use the instrument with one hand thus freeing his other hand for other purposes during the surgery. The present instrument overcomes many of the disadvantages encountered with prior art devices and provides a precision instrument which is easy to handle and simple to manufacture. While the invention has been particularly shown and described with reference to the preferred embodiments, it will be understood by those skilled in the art that various modifications in form and detail may be made therein without departing from the scope and spirit of the invention. Accordingly, modifications such as those suggested above, but not limited thereto, are to be considered within the scope of the invention.

What is claimed is:

1. An endoscopic surgical cutting instrument comprising:
   (a) a handle assembly;
   (b) a body portion extending from said handle assembly and defining a generally central longitudinal axis; and
   (c) a pair of cutting blade members including a first blade member and a second blade member pivotally connected to each other to open and close about a common pivot axis in response to movement of said handle assembly, each cutting blade member having a cutting edge which faces the cutting edge of the other cutting blade member and a generally curved crescent-shaped cross-section in a plane defined by said pivot axis and said longitudinal axis; and
   wherein said generally crescent-shaped first blade member has a radius of curvature and said generally crescent-shaped second blade member has a radius of curvature, a center of the radius of curvature of said first blade member being offset from a center of the radius of curvature of said second blade member by a predetermined distance measured along said longitudinal axis such that said first and second blade members contact each other during opening and closing movement thereof.

2. An instrument according to claim 1, further comprising means for urging said blade members toward each other.

3. An instrument according to claim 1, wherein a first blade member is stationary and a second blade member is pivotable in response to movement of said handle assembly.

4. An instrument according to claim 1, wherein the radius of curvature of said first blade member at said cutting edge is equal to the radius of curvature of said second blade member at said cutting edge.

5. An instrument according to claim 1, wherein said blade members contact each other during opening and closing at a single contact point along a length of said cutting edges to enhance shearing of tissue and thereby to define a gap between said blade members from said pivot axis to said contact point.

6. An instrument according to claim 5, wherein said gap is between about 0.015 inches and 0.025 inches when said blade members are closed.

7. An instrument according to claim 1, wherein said body portion comprises an outer tube member and an inner rod member slidably positioned within said tube member, said inner rod operably connected to said handle assembly and said pair of blade members to open and close said blade members.

8. An instrument according to claim 7, wherein said blade members are secured about said common pivot axis to said outer tube member.

9. An instrument according to claim 1, wherein said center of said radius of curvature of said first blade member is offset from said center of said radius of curvature of said second blade member between about 0.025 inches and 0.040 inches.

10. An instrument according to claim 9, wherein said centers of said radii of curvature are offset about 0.032 inches.

11. An instrument according to claim 1, wherein said blade members contact each other progressively at a plurality locations during opening and closing movement thereof for enhancing shearing of tissue.

12. An instrument according to claim 11, wherein said tissue shearing enhancing means comprises an inside surface of each blade member being angled toward said cutting edge to define a relief angle, said inside surfaces of said blade members facing each other when said blade members are in said closed position.

13. An instrument according to claim 12, wherein said relief angle is less than 5°.

14. An instrument according to claim 12, wherein said relief angle is between 2° and 3°.

15. An instrument according to claim 12, further comprising means for urging said blade members toward each other.

16. An instrument according to claim 15, wherein said blade member urging means comprises a spring washer.

17. An endoscopic surgical cutting instrument comprising:
   a) a handle assembly;
   b) a body portion extending from said handle assembly and defining a generally central longitudinal axis; and
   c) a pair of cutting blade members including a first blade member and a second blade member, pivotally connected to each other and being operable to open and close about a common pivot axis in response to movement of said handle assembly, said first blade member having a top edge and an opposed bottom cutting edge, and said second blade member having a bottom edge and an opposed top cutting edge, said blade members being positioned at an end of said body portion opposite said handle assembly and having generally curved crescent-shaped cross-sections in a plane defined by said pivot axis and said longitudinal axis;
   wherein said generally crescent-shaped blade members each has an inside surface facing each other when in a closed position, said inside surface of said first blade member being angled from said top edge toward said bottom cutting edge to define a first relief angle, said inside surface of said second blade member being angled from said bottom edge toward said top cutting edge to define a second relief angle, said first and second relief angles cooperating to maintain said bottom cutting edge of said first blade member in contact with said top cutting edge of said second blade member during opening and closing of said blade members.

18. An instrument according to claim 17, wherein said relief angle is less than 5°.

19. An instrument according to 17, wherein said relief angle is between 2° and 3°.

20. An instrument according to claim 17, wherein said blade members are metal injection molded and said relief angle is ground into said blade members after molding of said blade members to enhance shearing action of said blade members.

21. An instrument according to claim 17, wherein said blade members have different centers of radii of curvature relative to said common pivot axis, said centers of said radii of curvature being offset a predetermined distance along said longitudinal axis, such that during opening and closing said cutting edges contact at a single point to enhance shearing of tissue.

22. An instrument according to claim 21, wherein said blade members contact each other during opening and closing at said single point to define a gap between said blade members from said pivot axis to said contact point.

23. An endoscopic surgical instrument comprising:
   a) a handle assembly;
   b) a body portion extending from said handle assembly defining a longitudinal axis of said instrument; and
   c) a pair of cutting blade members including a first blade member and a second blade member connected to each other to open and close about a common pivot axis in response to movement of said handle assembly, each cutting blade member having a cutting edge which faces the cutting edge of the other cutting blade member and a generally curved crescent-shaped cross-section in a plane defined by said pivot axis and said longitudinal axis;

wherein said first curved generally crescent-shaped blade member has a first radius of curvature and said second curved generally crescent-shaped blade member has a second radius of curvature, said first and second radii of curvature being unequal, a center of said first radius of curvature being offset from a center of said second radius of curvature by a predetermined distance measured along said longitudinal axis, such that during opening and closing of said blade members, said first blade member contacts said second blade member progressively along a length of said cutting edges in a manner to enhance shearing of tissue.

24. An instrument according to claim 23, wherein said cutting edge of said first cutting blade member is defined by said first radius of curvature and said cutting edge of said second blade member is defined by said second radius of curvature.

* * * * *